(12) United States Patent
Tsuyuki

(10) Patent No.: US 10,874,365 B2
(45) Date of Patent: Dec. 29, 2020

(54) MEDICAL IMAGE DIAGNOSIS APPARATUS AND MEDICAL IMAGE PROCESSING METHOD

(71) Applicant: CANON MEDICAL SYSTEMS CORPORATION, Otawara (JP)

(72) Inventor: Masaharu Tsuyuki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 39 days.

(21) Appl. No.: 16/233,190

(22) Filed: Dec. 27, 2018

(65) Prior Publication Data
US 2019/0200945 A1 Jul. 4, 2019

(30) Foreign Application Priority Data
Dec. 28, 2017 (JP) .................. 2017-253484

(51) Int. Cl.
*A61B 6/00* (2006.01)
*A61B 6/03* (2006.01)
(Continued)

(52) U.S. Cl.
CPC ............ *A61B 6/4435* (2013.01); *A61B 6/032* (2013.01); *A61B 6/0487* (2020.08);
(Continued)

(58) Field of Classification Search
CPC ......... A61B 34/30; A61B 34/20; A61B 34/10; A61B 2090/3983; A61B 34/25; A61B 34/32; A61B 34/00; A61B 90/37
See application file for complete search history.

(56) References Cited

U.S. PATENT DOCUMENTS

2006/0149418 A1* 7/2006 Anvari ................... A61G 13/10
700/245
2009/0003975 A1* 1/2009 Kuduvalli ............ A61N 5/1049
414/146
(Continued)

FOREIGN PATENT DOCUMENTS

JP 2012-200463 10/2012
JP 2013-178247 9/2013
(Continued)

*Primary Examiner* — David P Porta
*Assistant Examiner* — Fani Boosalis
(74) *Attorney, Agent, or Firm* — Oblon, McClelland, Maier & Neustadt, L.L.P.

(57) ABSTRACT

A medical image diagnosis apparatus according to an embodiment obtains a first position of a predetermined part of an image taking target included in a medical robot system, a first direction of a rotation axis of the image taking target, and a first rotation angle of the image taking target, within a coordinate system of the medical image diagnosis apparatus. The medical image diagnosis apparatus derives information that brings the coordinate system of the medical image diagnosis apparatus and the coordinate system of the medical robot system into correspondence with each other, on the basis of the first position, the first direction, and the first rotation angle, as well as a second position of the predetermined part, a second direction of the rotation axis, and a second rotation angle of the image taking target, within a coordinate system of the medical robot system.

16 Claims, 12 Drawing Sheets

(51) Int. Cl.
- *A61B 34/30* (2016.01)
- *A61B 6/04* (2006.01)
- *A61B 6/10* (2006.01)
- *A61B 90/00* (2016.01)

(52) U.S. Cl.
CPC .......... *A61B 6/4458* (2013.01); *A61B 6/5205* (2013.01); *A61B 6/5223* (2013.01); *A61B 6/547* (2013.01); *A61B 6/587* (2013.01); *A61B 34/30* (2016.02); *A61B 6/102* (2013.01); *A61B 6/4035* (2013.01); *A61B 2090/3966* (2016.02)

(56) References Cited

U.S. PATENT DOCUMENTS

| | | |
|---|---|---|
| 2013/0225994 A1 | 8/2013 | Hsu et al. |
| 2014/0135611 A1* | 5/2014 | Loustaudaudine ...... B25J 9/045 600/407 |
| 2016/0220218 A1 | 8/2016 | Zaiki et al. |
| 2020/0078097 A1* | 3/2020 | Gregerson ......... A61B 17/3423 |

FOREIGN PATENT DOCUMENTS

| | | |
|---|---|---|
| JP | 2014-151114 | 8/2014 |
| JP | 2016-140668 | 8/2016 |

* cited by examiner

MEDICAL IMAGE DIAGNOSIS APPARATUS AND MEDICAL IMAGE PROCESSING METHOD

CROSS-REFERENCE TO RELATED APPLICATIONS

This application is based upon and claims the benefit of priority from Japanese Patent Application No. 2017-253484, filed on Dec. 28, 2017; the entire contents of which are incorporated herein by reference.

FIELD

Embodiments described herein relate generally to a medical image diagnosis apparatus and a medical image processing method.

BACKGROUND

There are peripheral devices (e.g., robots) that perform a manipulation such as a biopsy on an examined subject. For example, a peripheral device is configured to perform a biopsy by moving a puncture needle through a passage designated on a Computed Tomography (CT) image or a Multi Planar Reconstruction (MPR) image taken on an axial cross-sectional plane of the examined subject during an image taking process performed by a medical image diagnosis apparatus such as an X-ray CT apparatus.

To perform the manipulation accurately, it is necessary to align a coordinate system of the medical image diagnosis apparatus and a coordinate system of the peripheral device with each other.

DETAILED DESCRIPTION

A medical image diagnosis apparatus according to an embodiment includes processing circuitry. The processing circuitry is configured to obtain a first position of a predetermined part of an image taking target, a first direction of a rotation axis of the image taking target, and a first rotation angle of the image taking target, within a coordinate system of the medical image diagnosis apparatus, on the basis of image data acquired by imaging the image taking target that is one selected from between a robot arm included in a medical robot system and holding a medical tool and an object held by the robot arm. The processing circuitry is configured to obtain a second position of the predetermined part, a second direction of the rotation axis, and a second rotation angle of the image taking target, within a coordinate system of the medical robot system. The processing circuitry is configured to derive information that brings the coordinate system of the medical image diagnosis apparatus and the coordinate system of the medical robot system into correspondence with each other, on the basis of the first position, the first direction, the first rotation angle, the second position, the second direction, and the second rotation angle.

Exemplary embodiments of a medical image diagnosis apparatus and a medical image processing method will be explained below, with reference to the accompanying drawings. It is possible, in principle, to apply the description of each of the embodiments similarly to any other embodiment.

First Embodiment

Figure 1:
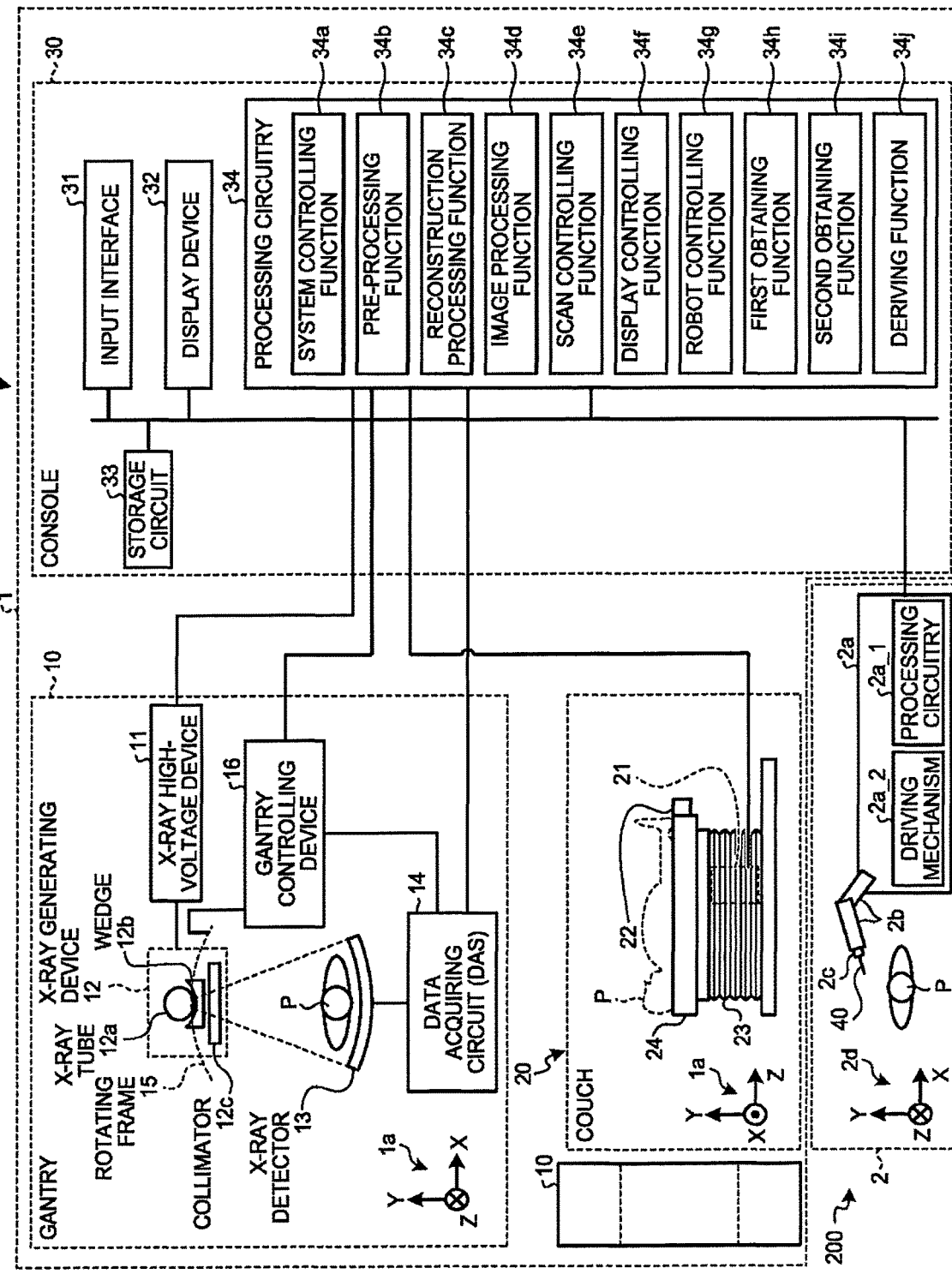
FIG. 1 is a diagram illustrating an exemplary configuration of an image taking system according to a first embodiment.

FIG. 1 is a diagram illustrating an exemplary configuration of an image taking system 100 according to a first embodiment. As illustrated in FIG. 1, the image taking system 100 according to the first embodiment includes an X-ray CT apparatus 1, and a medical robot system 200. The X-ray CT apparatus 1 is an example of the medical image diagnosis apparatus.

The X-ray CT apparatus 1 may be, for example, an Area Detector CT (ADCT) apparatus. The X-ray CT apparatus 1 includes a gantry 10, a couch 20, and a console 30. In the X-ray CT apparatus 1, a coordinate system 1a structured with an X-axis, a Y-axis, and a Z-axis is defined. In other words, the coordinate system 1a is an orthogonal coordinate system and is a coordinate system of the X-ray CT apparatus 1. The X-axis structuring the coordinate system 1a expresses a direction parallel to the floor surface. The Y-axis expresses a direction perpendicular to the floor surface. The Z-axis expresses either the direction of a rotation center axis of a rotating frame 15 (explained later) while the gantry 10 is in a non-tilted state or the longitudinal direction of a couchtop 22 of the couch 20.

The gantry 10 is a device configured to radiate X-rays onto an examined subject (hereinafter, "patient") P and to acquire data related to X-rays that have passed through the patient P. The gantry 10 includes an X-ray high-voltage device 11, an X-ray generating device 12, an X-ray detector 13, a data acquiring circuit 14, the rotating frame 15, and a gantry controlling device 16. When the gantry controlling device 16 exercises tilting control thereon, the gantry 10 is configured to rotate on the X-axis (to roll), to rotate on the Y-axis (to pitch), and to rotate on the Z-axis (to yaw).

The rotating frame 15 is an annular frame configured to support the X-ray generating device 12 and the X-ray detector 13 so as to oppose each other while the patient P is interposed therebetween and to rotate at a high speed on a circular orbit centered on the patient P under control exercised by the gantry controlling device 16.

The X-ray generating device 12 is a device configured to generate the X-rays and to radiate the generated X-rays onto the patient P. The X-ray generating device 12 includes an X-ray tube 12a, a wedge 12b, and a collimator 12c.

The X-ray tube 12a is a vacuum tube configured to emit thermo electrons from a negative pole (which may be referred to as a filament) to a positive pole (a target), by receiving a supply of high voltage from the X-ray high-voltage device 11. The X-ray tube 12a radiates an X-ray beam onto the patient P, as the rotating frame 15 rotates. In other words, the X-ray tube 12a is configured to generate the X-rays by using the high voltage supplied thereto from the X-ray high-voltage device 11.

Further, the X-ray tube 12a is configured to generate the X-ray beam that spreads with a fan angle and a cone angle. For example, under control of the X-ray high-voltage device 11, the X-ray tube 12a is capable of continuously emitting X-rays in the entire surrounding of the patient P to realize a full reconstruction process and is capable of continuously emitting X-rays in an emission range (180 degrees+the fan angle) that enables a half reconstruction to realize a half reconstruction process. Further, under the control of the X-ray high-voltage device 11, the X-ray tube 12a is capable of intermittently emitting X-rays (pulse X-rays) in positions (X-ray tube positions) set in advance. Further, the X-ray high-voltage device 11 is also capable of modulating intensities of the X-rays emitted from the X-ray tube 12a.

The wedge 12b is an X-ray filter configured to adjust the X-ray dose of the X-rays emitted from the X-ray tube 12a. More specifically, the wedge 12b is a filter configured to pass and attenuate the X-rays emitted from the X-ray tube 12a, so that the X-rays radiated from the X-ray tube 12a onto the patient P have a predetermined distribution. For example, the wedge 12b is a filter obtained by processing aluminum so as to have a predetermined target angle and a predetermined thickness. The wedge may be referred to as a wedge filter or a bow-tie filter.

The collimator 12c is configured by using a lead plate or the like and has a slit in a part thereof. For example, by using the slit, the collimator 12c is configured to narrow down the radiation range of the X-rays of which the X-ray dose has been adjusted by the wedge 12b, under the control of the X-ray high-voltage device 11.

Possible X-ray sources of the X-ray generating device 12 are not limited to the X-ray tube 12a. For example, in place of the X-ray tube 12a, the X-ray generating device 12 may be structured with a focus coil configured to converge an electron beam generated by an electron gun, a deflection coil configured to electromagnetically deflect the electron beam, and a target ring that covers a half of the surrounding of the patient P and is configured to generate X-rays by having the deflected electron beam collide thereon.

The X-ray high-voltage device 11 is structured with: a high-voltage generating device that is configured by using an electric circuit such as a transformer, a rectifier, and the like and that has a function of generating the high voltage to be applied to the X-ray tube 12a; and an X-ray controlling device configured to control the output voltage in accordance with the X-rays to be radiated by the X-ray tube 12a. The high-voltage generating device may be of a transformer type or of an inverter type. For example, by adjusting the X-ray tube voltage and the X-ray tube current supplied to the X-ray tube 12a, the X-ray high-voltage device 11 adjusts the dose of the X-rays radiated onto the patient P. Further, the X-ray high-voltage device 11 operates as described above, under control of processing circuitry 34 included in the console 30.

The gantry controlling device 16 is structured with: processing circuitry configured by using a processor or the like; and a driving mechanism configured by using a motor, an actuator, and the like. The gantry controlling device 16 has a function of controlling operations of the gantry 10 by receiving an input signal from either an input interface 31 (explained later) included in the console 30 or an input interface attached to the gantry 10. For example, the gantry controlling device 16 exercises control to cause the X-ray tube 12a and the X-ray detector 13 to revolve on a circular orbit centered on the patient P, by rotating the rotating frame 15 upon receipt of the input signal. As another example, the gantry controlling device 16 exercises control to tilt the gantry 10. The gantry controlling device 16 operates as described above under the control of the processing circuitry 34 included in the console 30.

The X-ray detector 13 is a two-dimensional array detector (an area detector) configured to detect the X-rays that have passed through the patient P. For example, the X-ray detector 13 has a structure in which a plurality of rows of X-ray detecting elements are arranged in the slice direction, while each of the rows of X-ray detecting elements includes a plurality of X-ray detecting elements that are arranged in a channel direction along an arc centered on a focal point of the X-ray tube 12a. The X-ray detecting elements included in the X-ray detector 13 are configured to detect the X-rays that were radiated from the X-ray generating device 12 and have passed through the patient P and are each configured to output an electrical signal (a pulse) corresponding to an X-ray dose to the data acquiring circuit 14. In this situation, the electrical signals output by the X-ray detector 13 may be referred to as detection signals.

The data acquiring circuit 14 (a Data Acquisition System [DAS]) is a circuit configured to acquire the detection signals output from the X-ray detecting elements included in the X-ray detector 13, to generate detection data from the acquired detection signals, and to output the generated detection data to the console 30.

In this situation, data obtained by applying one or more pre-processing processes such as a logarithmic conversion process, an offset correcting process, an inter-channel sensitivity correcting process, an inter-channel gain correcting process, a pile-up correcting process, a beam hardening correcting process, and/or the like to the detection data may be referred to as raw data. Further, the detection data and the raw data may collectively be referred to as projection data.

The couch 20 is a device on which the patient P to be scanned is placed and is configured to move the patient P placed thereon. The couch 20 includes a couch driving device 21, the couchtop 22, a pedestal 23, and a base (a supporting frame) 24.

The couchtop 22 is a plate-like member on which the patient P is placed. The base 24 is configured to support the couchtop 22. The pedestal 23 is a casing configured to support the base 24 in such a manner that the base 24 is able to move in directions perpendicular to the floor surface. The couch driving device 21 is either a motor or an actuator configured to move the patient P to the inside of the rotating frame 15 by moving the couchtop 22 on which the patient P is placed, in a longitudinal direction of the couchtop 22 (the Z-axis direction in the coordinate system 1a). In addition, the couch driving device 21 is also capable of moving the couchtop 22 in the X-axis directions.

As for methods of moving the couchtop 22, it is acceptable to move only the couchtop 22. Alternatively, it is also acceptable to move the couch 20 from the base 24 together therewith. Further, when the X-ray CT apparatus 1 is a standing CT apparatus, other methods are also acceptable in which the gantry 10 is moved in up-and-down directions (the directions perpendicular to the floor surface), in which a patient moving mechanism corresponding to the couchtop 22 is moved, or in which both the gantry 10 and a patient moving mechanism are moved.

For example, the gantry 10 is configured to perform a conventional scan by which the patient P is scanned on a circular orbit by causing the rotating frame 15 to rotate, while the position of the patient P is being fixed after the couchtop 22 is moved. Alternatively, the gantry 10 may perform a helical scan by which the patient P is helically scanned by causing the rotating frame 15 to rotate while the couchtop 22 is being moved. In these situations, the relative position between the gantry 10 and the couchtop 22 may be changed by controlling the moving of the couchtop 22. Further, when the gantry 10 is self-propelled, the relative position between the gantry 10 and the couchtop 22 may be changed by controlling the self-propelled movement of the gantry 10. Alternatively, the relative position between the gantry 10 and the couchtop 22 may be changed by controlling the self-propelled movement of the gantry 10 and the moving of the couchtop 22. In other words, the relationship of the relative position between the patient P placed on the couchtop 22 and the gantry 10 may be established by one or both of the self-propelled movement of the gantry 10 and the moving of the couchtop 22.

The console 30 is a device configured to receive operations performed by an operator on the X-ray CT apparatus 1 and to reconstruct X-ray CT image data by using the detection data output from the gantry 10. X-ray CT images may simply be referred to as CT images. As illustrated in FIG. 1, the console 30 includes the input interface 31, a display device 32, a storage circuit 33, and the processing circuitry 34.

The input interface 31 is configured to receive various types of input operations from the operator, to convert the received input operations into electrical signals, and to output the electrical signals to the processing circuitry 34. For example, the input interface 31 receives, from the operator, an acquisition condition used for acquiring the detection data, a reconstruction condition used for reconstructing CT image data, an image processing condition used for generating a post-processing image from the CT image data, and the like. For example, the input interface 31 is realized with a mouse, a keyboard, a trackball, a switch, a button, a joystick, and/or the like.

The display device 32 is configured to display various types of information. For example, the display device 32 is configured to output a medical image (a CT image) generated by the processing circuitry 34, a Graphical User Interface (GUI) used for receiving various types of operations from the operator, and the like. For example, the display device 32 may be a liquid crystal display device, a Cathode Ray Tube (CRT) display device, or the like.

The storage circuit 33 is realized by using, for example, a semiconductor memory element such as a Random Access Memory (RAM), a flash memory, or the like, a hard disk, an optical disk, or the like. For example, the storage circuit 33 is configured to store therein the detection data, the raw data, the CT image data, and the like.

The processing circuitry 34 includes, for example, a system controlling function 34a, a pre-processing function 34b, a reconstruction processing function 34c, an image processing function 34d, a scan controlling function 34e, a display controlling function 34f, a robot controlling function 34g, a first obtaining function 34h, a second obtaining function 34i, and a deriving function 34j. In this situation, for example, processing functions executed by the constituent elements of the processing circuitry 34 illustrated in FIG. 1, namely, the system controlling function 34a, the pre-processing function 34b, the reconstruction processing function 34c, the image processing function 34d, the scan controlling function 34e, the display controlling function 34f, the robot controlling function 34g, the first obtaining function 34h, the second obtaining function 34i, and the deriving function 34j, are recorded in the storage circuit 33 in the form of computer-executable programs. For example, the processing circuitry 34 is a processor and is configured to realize the functions corresponding to the programs by reading and executing the programs from the storage circuit 33. In other words, the processing circuitry 34 that has read the programs has the functions illustrated within the processing circuitry 34 in FIG. 1.

The system controlling function 34a is configured to control various types of functions of the processing circuitry 34 on the basis of the input operations received from the operator via the input interface 31.

The pre-processing function 34b is configured to generate the raw data by performing, on the detection data output from the data acquiring circuit 14, one or more pre-processing processes such as a logarithmic conversion process, an offset correcting process, an inter-channel sensitivity correcting process, a beam hardening correcting process, and/or the like. The pre-processing function 34b stores the generated raw data into the storage circuit 33.

The reconstruction processing function 34c is configured to reconstruct (generate) the CT image data by performing a reconstructing process that uses a filter correction back projection method or a successive approximation reconstruction method on the raw data generated by the pre-processing function 34b. For example, the reconstruction processing function 34c reconstructs CT image data that is three-dimensional (three-dimensional CT image data, volume data) by obtaining the raw data stored in the storage circuit 33 and performing the reconstructing process on the obtained raw data. The reconstruction processing function 34c stores the reconstructed CT image data into the storage circuit 33.

To reconstruct the CT image data, the reconstruction processing function 34c is able to use a full-scan reconstruction scheme and a half-scan reconstruction scheme. For example, when using the full-scan reconstruction scheme, the reconstruction processing function 34c requires raw data from the entire surrounding of the patient corresponding to 360 degrees. In contrast, when using the half-scan reconstruction scheme, the reconstruction processing function 34c requires raw data corresponding to 180 degrees+a fan angle.

The image processing function 34d is configured to convert the CT image data reconstructed by the reconstruction processing function 34c into image data of an MPR image or the like by using a publicly-known method, on the basis of an input operation received from the operator via the input interface 31. The image processing function 34d stores the image data resulting from the conversion into the storage circuit 33.

The scan controlling function 34e is configured to control a CT scan performed by the gantry 10. For example, the scan controlling function 34e controls execution of various types of scans performed by the gantry 10, by controlling operations of the X-ray high-voltage device 11, the X-ray detector 13, the gantry controlling device 16, the data acquiring circuit 14, and the couch driving device 21.

More specifically, the scan controlling function 34e is configured to control projection data acquiring processes in an image taking process to acquire a position determining image (a scanogram image, a scanogram) and a main image taking process (a scan) to acquire an image used for a diagnosis purpose. As a result of the scan controlling function 34e controlling the projection data acquiring processes, the X-ray CT apparatus 1 acquires the CT image data.

For example, the scan controlling function 34e causes a conventional scan or a helical scan to be executed. As a result, the X-ray CT apparatus 1 acquires the three-dimensional CT image data.

The display controlling function 34f is configured to exercise control so that the display device 32 displays any of various types of images represented by the various types of image data stored in the storage circuit 33.

The robot controlling function 34g is configured to control operations of a robot 2 (explained later). For example, the robot controlling function 34g causes the robot 2 to perform a manipulation such as a biopsy on the patient P. For example, the robot controlling function 34g causes the display device 32 to display a CT image or an MPR image taken on an axial cross-sectional plane of the patient P. After that, the robot controlling function 34g receives a passage designated by the user in the CT image or the MPR image. Further, the robot controlling function 34g transmits position information of a plurality of points structuring the received passage to the robot 2 and controls operations of the robot 2 so as to perform the biopsy by moving a puncture needle 40 (explained later). In other words, the robot controlling function 34g controls operations of the robot 2 so as to insert the puncture needle 40 (explained later) into the patient P. In this situation, the robot controlling function 34g transmits the position information of the plurality of points in the coordinate system 1a, to the robot 2. In this manner, the robot controlling function 34g controls the operations of the robot 2 completely automatically.

In this situation, the robot controlling function 34g may control the operations of the robot 2 through a remote operation performed by the operator. For example, as a result of the operator operating the input interface 31 or a lever (not illustrated), an instruction that causes the robot 2 to operate is input to the processing circuitry 34. When the instruction has been input to the processing circuitry 34, the robot controlling function 34g controls operations of the robot 2 according to the instruction.

The first obtaining function 34h, the second obtaining function 34i, and the deriving function 34j are configured to perform a coordinate system aligning process. Details of the first obtaining function 34h, the second obtaining function 34i, and the deriving function 34j will be explained later. The first obtaining function 34h is an example of a first obtaining unit and an obtaining unit. The second obtaining function 34i is an example of a second obtaining unit. The deriving function 34j is an example of a deriving unit.

The medical robot system 200 includes the robot 2. The robot 2 is installed with the X-ray CT apparatus 1. For example, the robot 2 may be attached to either the couchtop 22 or the gantry 10. Alternatively, the robot 2 may be mounted (fixed) onto the floor on which the couch 20 is placed, in the vicinity of the couch 20.

The robot 2 is configured to perform manipulations such as a biopsy. The robot 2 includes a robot main body 2a, a robot arm 2b, and a holding unit 2c. When a manipulation such as a biopsy is performed, the holding unit 2c holds the puncture needle 40. Accordingly, the robot arm 2b holds the puncture needle 40 via the holding unit 2c. The puncture needle 40 is an example of the medical tool. In a tip end part of the robot arm 2b, the holding unit 2c is rotatably attached to the robot arm 2b.

The robot main body 2a is configured to support the robot arm 2b while allowing the robot arm 2b to perform operations. The robot main body 2a includes processing circuitry 2a_1 configured by using a processor or the like and a driving mechanism 2a_2 configured by using a motor and an actuator or the like and configured to cause the robot arm 2b and the holding unit 2c to operate. For example, on the basis of the position information of the plurality of points transmitted thereto from the robot controlling function 34g, the processing circuitry 2a_1 is configured to control operations of the robot arm 2b and the holding unit 2c, so that the puncture needle 40 is inserted into the patient P through the passage structured by the plurality of points. More specifically, the processing circuitry 2a_1 controls the operations of the robot arm 2b and the holding unit 2c, by controlling the driving mechanism 2a_2.

The term "processor" used in the explanations above denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions thereof by reading programs saved in a storage circuit and executing the read programs. In this situation, instead of saving the programs in the storage circuit, it is also acceptable to directly incorporate the programs in the circuits of the processors. In that situation, the processors realize the functions thereof by reading the programs incorporated in the circuits thereof and executing the read programs. Further, the one or more processors in the present embodiments do not each necessarily have to be structured as a single circuit. It is also acceptable to structure one processor by combining together a plurality of independent circuits so as to realize the functions thereof.

Figure 2:
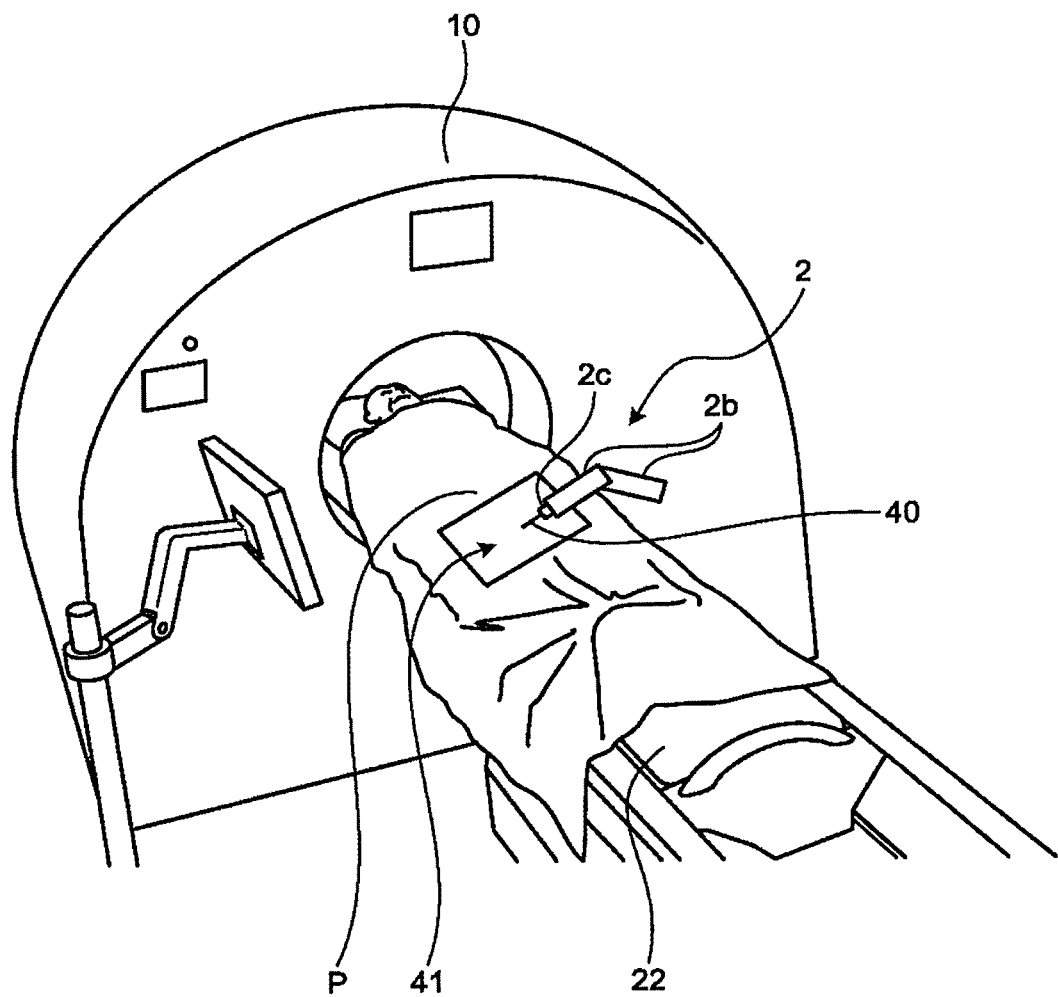
FIG. 2 is a drawing for explaining an example of an operation performed by a robot according to the first embodiment.

FIG. 2 is a drawing for explaining an example of an operation performed by the robot 2 according to the first embodiment. As illustrated in the example in FIG. 2, the processing circuitry 2a_1 controls operations of the robot arm 2b so that the puncture needle 40 is inserted into a puncture target site 41 of the patient P placed on the couchtop 22. The example in FIG. 2 illustrates only the robot arm 2b and the holding unit 2c among the constituent elements of the robot 2.

In this situation, in the medical robot system 200, a coordinate system 2d is defined. The processing circuitry 2a_1 controls operations of the robot arm 2b so that the puncture needle 40 is inserted into the patient P through the designated passage, in the coordinate system 2d of the medical robot system 200. The coordinate system 2d is an orthogonal coordinate system structured with an X-axis, a Y-axis, and a Z-axis.

Figure 3:
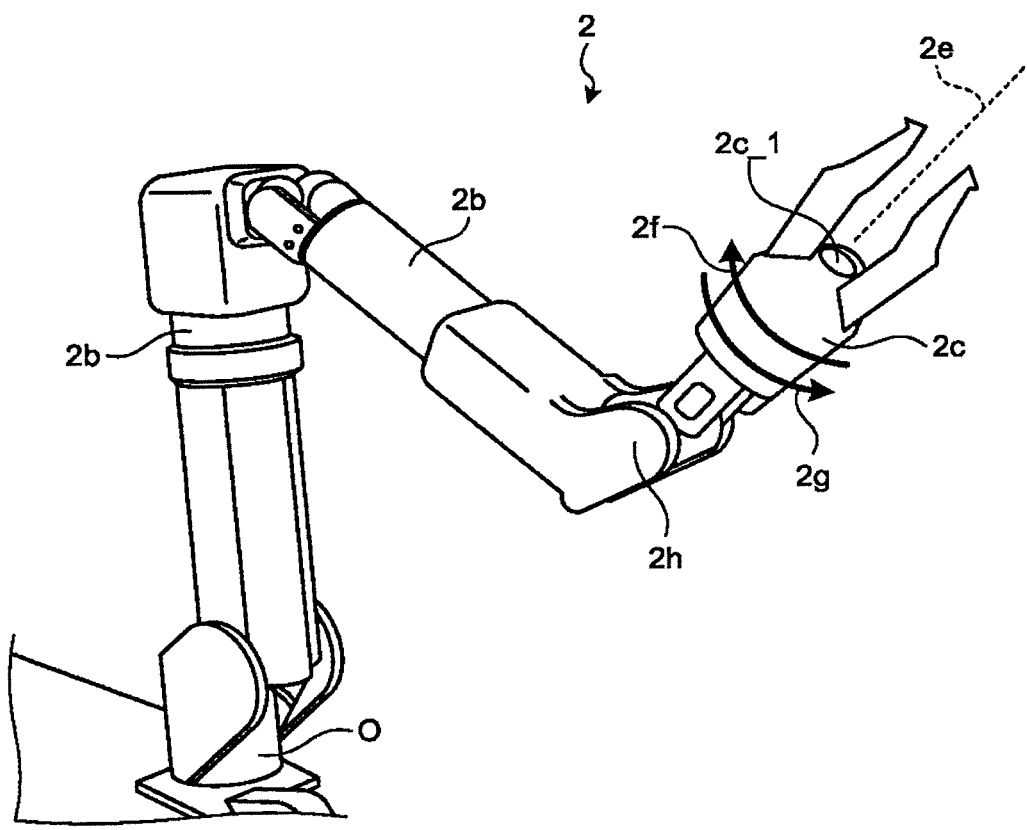
FIG. 3 is a drawing illustrating examples of a robot arm and a holding unit of the robot according to the first embodiment.

FIG. 3 is a drawing illustrating examples of the robot arm 2b and the holding unit 2c of the robot 2 according to the first embodiment. The robot arm 2b illustrated in the example in FIG. 3 performs operations and changes postures thereof, under the control of the processing circuitry 2a_1.

Further, the holding unit 2c illustrated in the example in FIG. 3 has formed therein an insertion opening 2c_1 through which the puncture needle 40 can be inserted. When the puncture needle 40 has been inserted in the insertion opening 2c_1, the puncture needle 40 is fixed to the holding unit 2c.

By the driving mechanism 2a_2, the holding unit 2c is caused to rotate around a rotation axis 2e, either in a first rotation direction 2f or in a second rotation direction 2g, which is the opposite direction of the first rotation direction 2f. Further, the holding unit 2c is configured to stop the rotation thereof in such a position where the rotation angle thereof becomes equal to a certain rotation angle with respect to a reference rotation angle (e.g., 0 degrees). When the holding unit 2c holding the puncture needle 40 rotates around the rotation axis 2e, it means that the puncture needle 40 also rotates. The rotation axis of the puncture needle 40 substantially coincides with the rotation axis 2e of the holding unit 2c.

In this situation, the processing circuitry 2a_1 learns the position (three-dimensional coordinates) of a predetermined part 2h of the robot arm 2b, the direction of the rotation axis 2e, and the rotation angle of the holding unit 2c, within the coordinate system 2d using a point O as the origin thereof, on the basis of an operation status of the driving mechanism 2a_2 and a detection signal from sensors attached to the robot arm 2b and to the holding unit 2c. In this situation, the direction of the rotation axis 2e may be, for example, the direction in which the rotation axis 2e extends.

The exemplary configuration of the image taking system 100 according to the first embodiment has thus been explained. The X-ray CT apparatus 1 according to the first embodiment structured as described above is configured to perform the coordinate system aligning process explained below, so as to be able to easily and conveniently align the coordinate system 1a of the X-ray CT apparatus 1 and the coordinate system 2d of the medical robot system 200 with each other.

Figure 4:
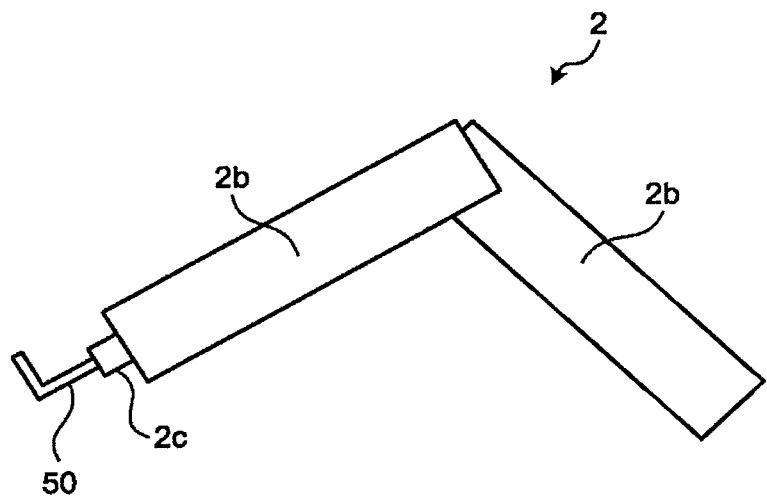
FIG. 4 is a drawing illustrating an example of an object according to the first embodiment.

FIG. 4 is a drawing illustrating an example of an object 50 according to the first embodiment. In the first embodiment, when the coordinate system aligning process is to be performed, the holding unit 2c holds the object 50 as illustrated in the example in FIG. 4.

Figure 5:
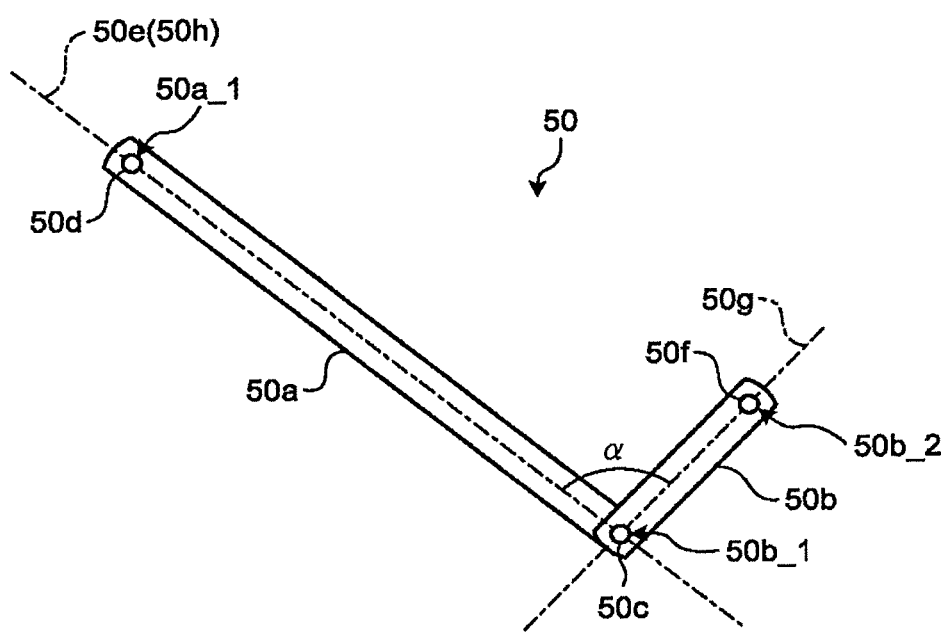
FIG. 5 is a drawing illustrating a specific example of the object according to the first embodiment.

FIG. 5 is a drawing illustrating a specific example of the object 50 according to the first embodiment. FIG. 5 is a top view of the object 50. The object 50 illustrated in the example in FIG. 5 includes members 50a and 50b. The members 50a and 50b are each a bar-like member having a circular cylindrical shape. One end of the member 50b is linked to one end of the member 50a.

As illustrated in the example in FIG. 5, a marker 50c is attached to a predetermined part 50b_1 of the member 50b that is positioned, in a top view, on a central axis 50e of the member 50a. Further, another marker 50d is attached to a predetermined part 50a_1 of the member 50a that is positioned, in a top view, on the central axis 50e. In other words, the markers 50c and 50d are attached to two locations on the central axis 50e. Accordingly, it is possible to identify the central axis 50e in the coordinate system 1a and to identify the direction of the central axis 50e, on the basis of the position of the marker 50c and the position of the marker 50d within the coordinate system 1a. The direction of the central axis 50e may be, for example, the direction in which the central axis 50e extends.

Further, as illustrated in the example in FIG. 5, yet another marker 50f is attached to a predetermined part 50b_2 of the member 50b that is positioned away from the marker 50c by a predetermined distance along the direction of a central axis 50g of the member 50b. For example, the marker 50f is attached in such a manner that, in a top view, an angle (a first angle) α formed by the central axis 50e of the member 50a and the central axis 50g of the member 50b is substantially equal to a second angle. The second angle is an angle formed by a line segment connecting the marker 50f to the marker 50c and another line segment connecting the marker 50c to the marker 50d. In other words, the predetermined part 50b_2 is determined so that the angle (the second angle) formed by a line segment connecting the predetermined part 50b_1 to the predetermined part 50b_2 and another line segment connecting the predetermined part 50b_1 to the predetermined part 50a_1 is substantially equal to the angle α. In the example illustrated in FIG. 5, the distance between the marker 50c and the marker 50d is different from the distance between the marker 50c and the marker 50f. For this reason, the positional relationship among the three markers 50c, 50d, and 50f is an axially asymmetric positional relationship. The axially asymmetric positional relationship denotes, for example, a positional relationship in which, even when the positioning pattern of the markers 50c, 50d, and 50f is inverted by using a certain straight line as an axis, the positioning pattern does not overlap with the inverted positioning pattern. Further, although the angle α is 90 degrees in the example illustrated in FIG. 5, the angle α may be an angle other than 90 degrees. Further, it is sufficient when the object 50 is provided with markers in at least three locations. More specifically, to be able to identify the direction of the central axis 50e, it is sufficient when the object 50 is provided with markers in a plurality of locations of which the quantity is at least three and which are not positioned on mutually the same straight line. In other words, the plurality of markers are not positioned on mutually the same straight line.

Further, it is sufficient when the positional relationship among the plurality of markers provided in at least three locations is an axially asymmetric positional relationship. For example, in the example illustrated in FIG. 5, if the distance between the marker 50c and the marker 50d were equal to the distance between the marker 50c and the marker 50f, the positional relationship among the markers 50c, 50d, and 50f would be an axially symmetric positional relationship that uses a straight line passing through the marker 50c as the axis of symmetry. Accordingly, in that situation, the object 50 is newly provided with a fourth marker so that the positional relationship among the four markers becomes an axially asymmetric positional relationship.

The markers 50c, 50d, and 50f may be formed by using, for example, a material of which the X-ray transmittance is either higher or lower than that of the materials used for structuring the robot arm 2b and the holding unit 2c.

On the basis of the position of the marker 50c, the position of the marker 50d, and the position of the marker 50f within the coordinate system 1a, it is possible to obtain the rotation angle, around the central axis 50e, of the line segment connecting the marker 50f to the marker 50c, the rotation angle being observed when the object 50 rotates while using the central axis 50e as the rotation axis thereof. Accordingly, on the basis of the position of the marker 50c, the position of the marker 50d, and the position of the marker 50f within the coordinate system 1a, it is possible to obtain the rotation angle, around the central axis 50e, of the member 50b that is observed within the coordinate system 1a when the object 50 rotates while using the central axis 50e as the rotation axis thereof. In other words, on the basis of the position of the marker 50c, the position of the marker 50d, and the position of the marker 50f within the coordinate system 1a, it is possible to obtain the rotation angle of the object 50 around the central axis 50e within the coordinate system 1a.

Further, the object 50 is held by the holding unit 2c in such a manner that the central axis 50e substantially coincides with the rotation axis 2e of the holding unit 2c. Accordingly, when the holding unit 2c rotates around the rotation axis 2e, the object 50 rotates while using the central axis 50e as the rotation axis thereof. In the explanations below, the rotation axis of the object 50 in that situation will be referred to as a "rotation axis 50h".

Figure 6:
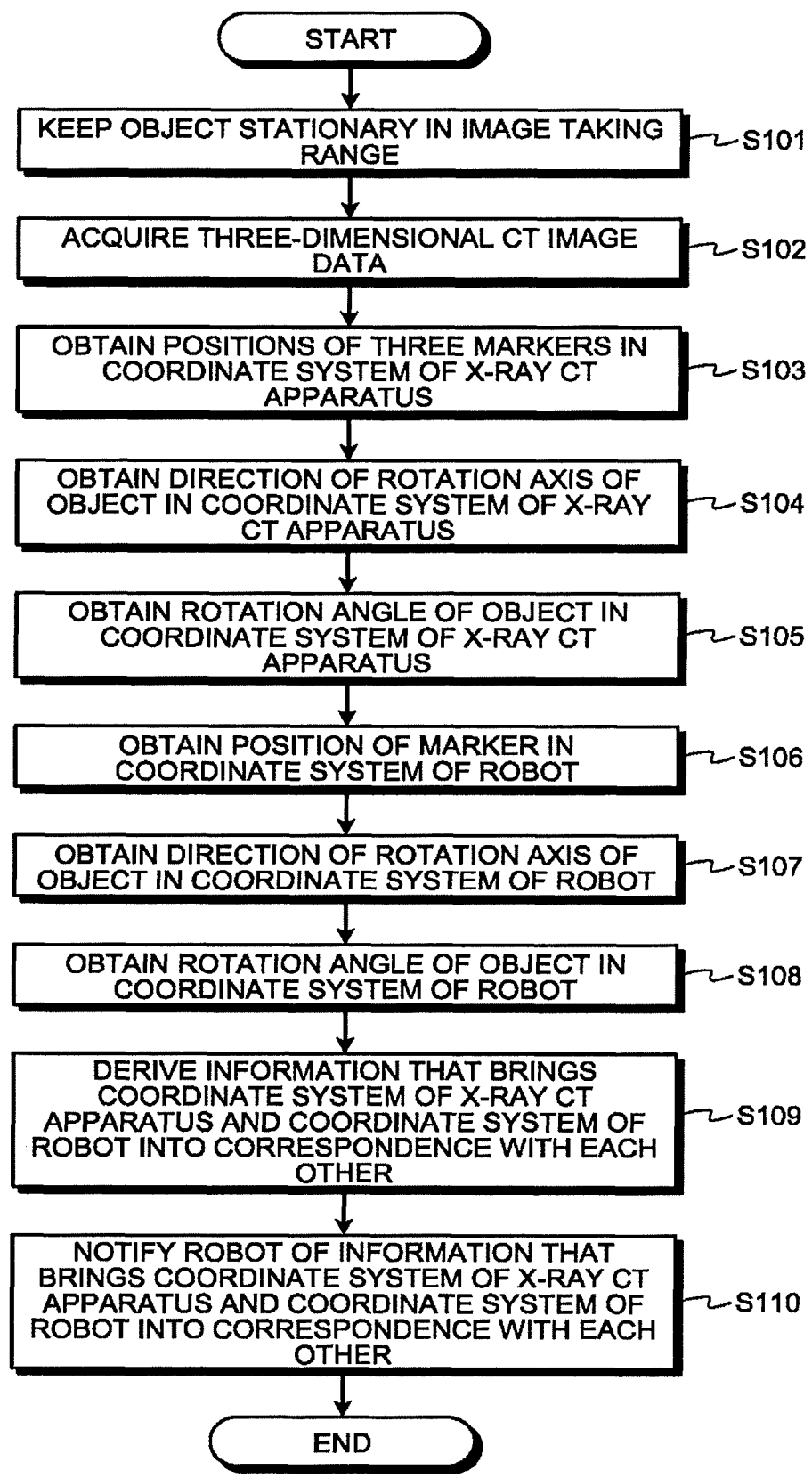
FIG. 6 is a flowchart illustrating a flow in an example of a coordinate system aligning process performed by an X-ray CT apparatus according to the first embodiment.

Next, an example of the coordinate system aligning process will be explained. FIG. 6 is a flowchart illustrating a flow in an example of the coordinate system aligning process performed by the X-ray CT apparatus 1 according to the first embodiment. The coordinate system aligning process is performed, for example, when the input interface 31 receives, from the user, an instruction to execute the coordinate system aligning process and further inputs the instruction to execute the coordinate system aligning process to the processing circuitry 34. When the coordinate system aligning process is to be executed, the patient P is not placed on the couch 20. Further, the coordinate system aligning process is an example of a process based on the medical image processing method.

As illustrated in FIG. 6, the robot controlling function 34g controls operations of the robot 2 and keeps the object 50 stationary in an image taking range (a scan range) of the gantry 10 so that the object 50 held by the holding unit 2c of the robot 2 is positioned in the image taking range (step S101).

After that, the scan controlling function 34e causes a conventional scan to be performed on the object 50 kept stationary in the image taking range, so that three-dimensional CT image data is acquired by the X-ray CT apparatus 1 (step S102). The acquired three-dimensional CT image data is an example of the image data. The object 50 is an example of the image taking target.

Subsequently, on the basis of the acquired three-dimensional CT image data, the first obtaining function 34h obtains the position of the marker 50c, the position of the marker 50d, and the position of the marker 50f (the positions of the three markers) within the coordinate system 1a (step S103). For example, at step S103, the first obtaining function 34h identifies the positions of the marker 50c, the marker 50d, and the marker 50f within a coordinate system of the three-dimensional CT image. After that, on the basis of a correspondence relationship that is known between coordinates within the coordinate system of the three-dimensional CT image and coordinates within the coordinate system 1a, the first obtaining function 34h obtains the positions of the marker 50c, the marker 50d, and the marker 50f within the coordinate system 1a, on the basis of the positions of the marker 50c, the marker 50d, and the marker 50f within the coordinate system of the three-dimensional CT image.

In this situation, the position of the marker 50c and the position of the predetermined part 50b_1 to which the marker 50c is attached are positioned close to each other. For this reason, the X-ray CT apparatus 1 is able to treat the position of the marker 50c as the position of the predetermined part 50b_1 to which the marker 50c is attached. For the same reason, the X-ray CT apparatus 1 is able to treat the position of the marker 50d as the position of the predetermined part 50a_1 to which the marker 50d is attached. Similarly, the X-ray CT apparatus 1 is able to treat the position of the marker 50f as the position of the predetermined part 50b_2 to which the marker 50f is attached. In this situation, the position of the marker 50c and the position of the predetermined part 50b_1 within the coordinate system 1a are each an example of the first position.

After that, on the basis of the position of the marker 50c and the position of the marker 50d within the coordinate system 1a, the first obtaining function 34h obtains the direction of the rotation axis 50h of the object 50 within the coordinate system 1a (step S104). For example, at step S104, on the basis of the position of the marker 50c and the position of the marker 50d within the coordinate system 1a, the first obtaining function 34h identifies the rotation axis 50h of the object 50 within the coordinate system 1a and further obtains the direction of the rotation axis 50h. The direction of the rotation axis 50h within the coordinate system 1a is an example of the first direction.

Subsequently, on the basis of the position of the marker 50c, the position of the marker 50d, and the position of the marker 50f within the coordinate system 1a, the first obtaining function 34h obtains the rotation angle of the object 50 within the coordinate system 1a (step S105). The rotation angle of the object 50 within the coordinate system 1a is an example of the first rotation angle.

After that, the second obtaining function 34i obtains the position of the marker 50c within the coordinate system 2d, from the robot 2 (step S106). In this situation, as explained above, the processing circuitry 2a_1 has learned the position (the three-dimensional coordinates) of the predetermined part 2h of the robot arm 2b within the coordinate system 2d. In addition, the processing circuitry 2a_1 has learned the positional relationship between the predetermined part 2h and the marker 50c within the coordinate system 2d. Accordingly, on the basis of the position of the predetermined part 2h and the positional relationship between the predetermined part 2h and the marker 50c, the processing circuitry 2a_1 is able to learn the position of the marker 50c within the coordinate system 2d.

Accordingly, at step S106, the second obtaining function 34i transmits a request to the processing circuitry 2a_1 of the robot 2 indicating that the position of the marker 50c within the coordinate system 2d should be transmitted. When having received the request, the processing circuitry 2a_1 transmits the position of the marker 50c within the coordinate system 2d to the processing circuitry 34. In this manner, the second obtaining function 34i obtains the position of the marker 50c within the coordinate system 2d, from the robot 2. In this situation, the position of the marker 50c and the position of the predetermined part 50b_1 within the coordinate system 2d are each an example of the second position.

Subsequently, the second obtaining function 34i obtains the direction of the rotation axis 50h of the object 50 within the coordinate system 2d, from the robot 2 (step S107). In this situation, as explained above, the processing circuitry 2a_1 has learned the direction of the rotation axis 2e within the coordinate system 2d. Also, the direction of the rotation axis 2e within the coordinate system 2d substantially coincides with the direction of the rotation axis 50h within the coordinate system 2d. Accordingly, the processing circuitry $2a\_1$ is able to treat the direction of the rotation axis $2e$ as the direction of the rotation axis $50h$.

Accordingly, at step S107, the second obtaining function $34i$ transmits a request to the processing circuitry $2a\_1$ of the robot 2 indicating that the direction of the rotation axis $50h$ within the coordinate system $2d$ should be transmitted. When having received the request, the processing circuitry $2a\_1$ transmits the direction of the rotation axis $2e$ within the coordinate system $2d$ as the direction of the rotation axis $50h$, to the processing circuitry 34. In this manner, the second obtaining function $34i$ has obtained the direction of the rotation axis $50h$ within the coordinate system $2d$, from the robot 2. The direction of the rotation axis $50h$ within the coordinate system $2d$ is an example of the second direction.

After that, the second obtaining function $34i$ obtains the rotation angle of the object 50 within the coordinate system $2d$, from the robot 2 (step S108). In this situation, as explained above, the processing circuitry $2a\_1$ has learned the rotation angle of the holding unit $2c$ within the coordinate system $2d$. Also, the processing circuitry $2a\_1$ has learned a shift amount of the rotation angle of the object 50 with respect to the rotation angle of the holding unit $2c$ within the coordinate system $2d$. Accordingly, on the basis of the rotation angle of the holding unit $2c$ and the shift amount of the rotation angle of the object 50 with respect to the rotation angle of the holding unit $2c$, the processing circuitry $2a\_1$ is able to learn the rotation angle of the object 50 within the coordinate system $2d$.

Accordingly, at step S108, the second obtaining function $34i$ transmits a request to the processing circuitry $2a\_1$ of the robot 2 indicating that the rotation angle of the object 50 within the coordinate system $2d$ should be transmitted. When having received the request, the processing circuitry $2a\_1$ transmits the rotation angle of the object 50 within the coordinate system $2d$ to the processing circuitry 34. In this manner, the second obtaining function $34i$ has obtained the rotation angle of the object 50 within the coordinate system $2d$, from the robot 2. The rotation angle of the object 50 within the coordinate system $2d$ is an example of the second rotation angle.

After that, on the basis of the position of the marker $50c$, the direction of the rotation axis $50h$ of the object 50, and the rotation angle of the object 50 within the coordinate system $1a$, as well as the position of the marker $50c$, the direction of the rotation axis $50h$ of the object 50, and the rotation angle of the object 50 within the coordinate system $2d$, the deriving function $34j$ derives information that brings the coordinate system $1a$ and the coordinate system $2d$ into correspondence with each other (step S109).

For example, at step S109, the deriving function $34j$ arranges the coordinate system $1a$ and the coordinate system $2d$ to substantially coincide with each other, by translating and rotating the coordinate system $2d$.

In a specific example, the deriving function $34j$ arranges the coordinate system $1a$ and the coordinate system $2d$ to substantially coincide with each other, by arranging the position of the marker $50c$ within the coordinate system $1a$ and the position of the marker $50c$ within the coordinate system $2d$ to substantially coincide with each other, arranging the direction of the rotation axis $50h$ within the coordinate system $1a$ and the direction of the rotation axis $50h$ within the coordinate system $2d$ to substantially coincide with each other, and arranging the rotation angle of the object 50 within the coordinate system $1a$ and the rotation angle of the object 50 within the coordinate system $2d$ to substantially coincide with each other.

After that, at step S109, the deriving function $34j$ derives a translation amount and a rotation amount of the coordinate system $2d$ that were used for arranging the coordinate system $1a$ and the coordinate system $2d$ to substantially coincide with each other, as information that brings the coordinate system $1a$ and the coordinate system $2d$ into correspondence with each other.

Subsequently, the deriving function $34j$ notifies the robot 2 of the information that brings the coordinate system $1a$ and the coordinate system $2d$ into correspondence with each other (step S110). After that, the deriving function $34j$ ends the coordinate system aligning process.

For example, when having received the information that brings the coordinate system $1a$ and the coordinate system $2d$ into correspondence with each other, the processing circuitry $2a\_1$ included in the robot 2 generates a transformation matrix used for transforming coordinates within the coordinate system $1a$ into coordinates within the coordinate system $2d$, by using the received information. By using the generated transformation matrix, the processing circuitry $2a\_1$ transforms the position information within the coordinate system $1a$ transmitted thereto from the robot controlling function $34g$, into position information within the coordinate system $2d$. After that, the processing circuitry $2a\_1$ controls the robot arm $2b$ and the holding unit $2c$ by using the position information within the coordinate system $2d$ resulting from the transformation. In this manner, the processing circuitry $2a\_1$ brings the coordinate system $1a$ and the coordinate system $2d$ into correspondence with each other.

Alternatively, the processing circuitry $2a\_1$ may correct the coordinate system $2d$ so as to substantially coincide with the coordinate system $1a$, by using the information that brings the coordinate system $1a$ and the coordinate system $2d$ into correspondence with each other. In a specific example, the processing circuitry $2a\_1$ translates the coordinate system $2d$ by the translation amount indicated in the received information. Further, the processing circuitry $2a\_1$ rotates the coordinate system $2d$ by the rotation amount indicated in the received information. The deriving function $34j$ may bring the coordinate system $1a$ and the coordinate system $2d$ into correspondence with each other in this manner.

Alternatively, the deriving function $34j$ may generate the transformation matrix described above, by using the information that brings the coordinate system $1a$ and the coordinate system $2d$ into correspondence with each other. After that, instead of transmitting the position information within the coordinate system $1a$ to the robot 2, the robot controlling function $34g$ may transform the position information within the coordinate system $1a$ into position information within the coordinate system $2d$ by using the transformation matrix and may further transmit the position information within the coordinate system $2d$ resulting from the transformation, to the robot 2.

Step S101 is a step corresponding to the robot controlling function $34g$. Step S101 is a step at which the robot controlling function $34g$ is realized as a result of the processing circuitry 34 reading and executing a predetermined program corresponding to the robot controlling function $34g$ from the storage circuit 33. Further, step S102 is a step corresponding to the scan controlling function $34e$. Step S102 is a step at which the scan controlling function $34e$ is realized as a result of the processing circuitry 34 reading and executing a predetermined program corresponding to the scan controlling function $34e$ from the storage circuit 33. Steps S103 through S105 are steps corresponding to the first obtaining function 34*h*. Steps S103 through S105 are steps at which the first obtaining function 34*h* is realized as a result of the processing circuitry 34 reading and executing a predetermined program corresponding to the first obtaining function 34*h* from the storage circuit 33. Steps S106 through S108 are steps corresponding to the second obtaining function 34*i*. Steps S106 through S108 are steps at which the second obtaining function 34*i* is realized as a result of the processing circuitry 34 reading and executing a predetermined program corresponding to the second obtaining function 34*i* from the storage circuit 33. Steps S109 and S110 are steps corresponding to the deriving function 34*j*. Steps S109 and S110 are steps at which the deriving function 34*j* is realized as a result of the processing circuitry 34 reading and executing a predetermined program corresponding to the deriving function 34*j* from the storage circuit 33.

In the coordinate system aligning process described above, the first obtaining function 34*h* obtains the position of the predetermined part 50*b*_1 of the object 50, the direction of the rotation axis 50*h* of the object 50, and the rotation angle of the object 50 within the coordinate system 1*a* of the X-ray CT apparatus 1, on the basis of the three-dimensional CT image data acquired by imaging the object 50 held by the robot 2. The second obtaining function 34*i* obtains the position of the predetermined part 50*b*_1, the direction of the rotation axis 50*h*, and the rotation angle of the object 50 within the coordinate system 2*d* of the medical robot system 200, from the robot 2. The deriving function 34*j* derives the information that brings the coordinate system 1*a* and the coordinate system 2*d* into correspondence with each other, on the basis of the position, the direction, and the rotation angle obtained by the first obtaining function 34*h*, as well as the position, the direction, the rotation angle obtained by the second obtaining function 34*i*.

Further, in the coordinate system aligning process described above, the first obtaining function 34*h* obtains the position of the predetermined part 50*b*_1 of the object 50, the direction of the rotation axis 50*h* of the object 50, and the rotation angle of the object 50 within the coordinate system 1*a* of the X-ray CT apparatus 1, on the basis of the three-dimensional CT image data acquired by imaging the plurality of markers 50*c*, 50*d*, and 50*f* provided in the three locations of the object 50.

In this manner, according to the first embodiment, it is possible to derive the information used for aligning the coordinate system 1*a* of the X-ray CT apparatus 1 and the coordinate system 2*d* of the medical robot system 200 with each other, without the need to have the user perform cumbersome operations. Consequently, according to the first embodiment, it is possible to easily and conveniently align the coordinate system 1*a* of the X-ray CT apparatus 1 and the coordinate system 2*d* of the medical robot system 200 with each other.

A First Modification Example of the First Embodiment

Next, a first modification example of the first embodiment will be explained. In the first embodiment described above, the example is explained in which the first obtaining function 34*h* obtains the position of the predetermined part 50*b*_1 of the object 50, the direction of the rotation axis 50*h* of the object 50, and the rotation angle of the object 50 within the coordinate system 1*a* of the X-ray CT apparatus 1, on the basis of the three-dimensional CT image data acquired by imaging the object 50.

In contrast, in the first modification example of the first embodiment, the X-ray CT apparatus 1 includes a visible light camera. Further, in the first modification example of the first embodiment, on the basis of image data acquired by imaging the object 50 while using the visible light camera, the first obtaining function 34*h* obtains the position of the predetermined part 50*b*_1 of the object 50, the direction of the rotation axis 50*h* of the object 50, and the rotation angle of the object 50, within the coordinate system 1*a* of the X-ray CT apparatus 1.

For example, on the basis of image data acquired by imaging markers provided in at least three positions that are not positioned on mutually the same straight line while using the visible light camera, the first obtaining function 34*h* obtains the position of the predetermined part 50*b*_1 of the object 50, the direction of the rotation axis 50*h* of the object 50, and the rotation angle of the object 50, within the coordinate system 1*a* of the X-ray CT apparatus 1. For example, when a stereo camera is used as the visible light camera, the first obtaining function 34*h* obtains the position of the predetermined part 50*b*_1 of the object 50, the direction of the rotation axis 50*h* of the object 50, and the rotation angle of the object 50, within the coordinate system 1*a* of the X-ray CT apparatus 1, on the basis of two pieces of image data acquired in one session of image taking process. A second modification example of the first embodiment In the first embodiment, the example is explained in which, at step S102 in the coordinate system aligning process, the X-ray CT apparatus 1 acquires the three-dimensional CT image data as a result of the scan controlling function 34*e* causing the conventional scan to be performed on the object 50 kept stationary in the image taking range. When a predetermined condition is satisfied, however, at step S102, the X-ray CT apparatus 1 may acquire the three-dimensional CT image data as a result of the scan controlling function 34*e* causing a helical scan to be performed on the object 50 kept stationary in the image taking range.

Figure 7:
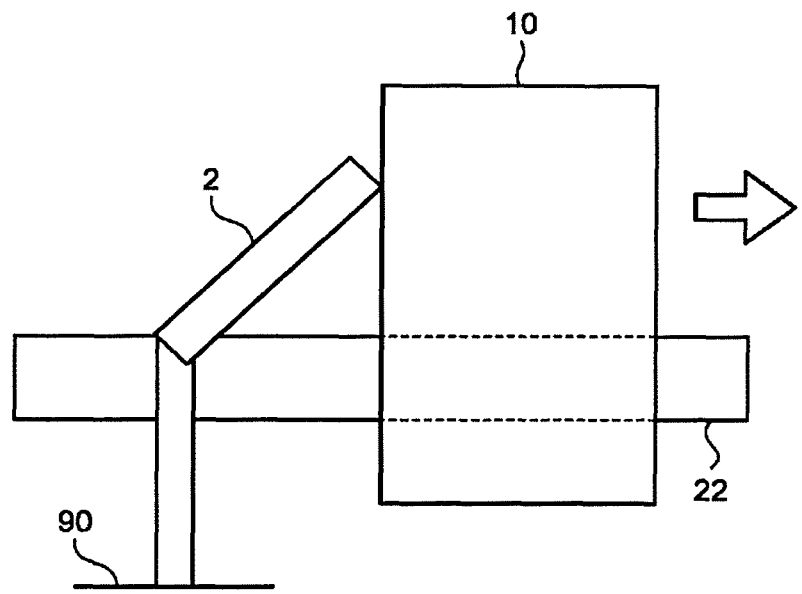
FIG. 7 is a drawing for explaining a second modification example of the first embodiment.
Figure 8:
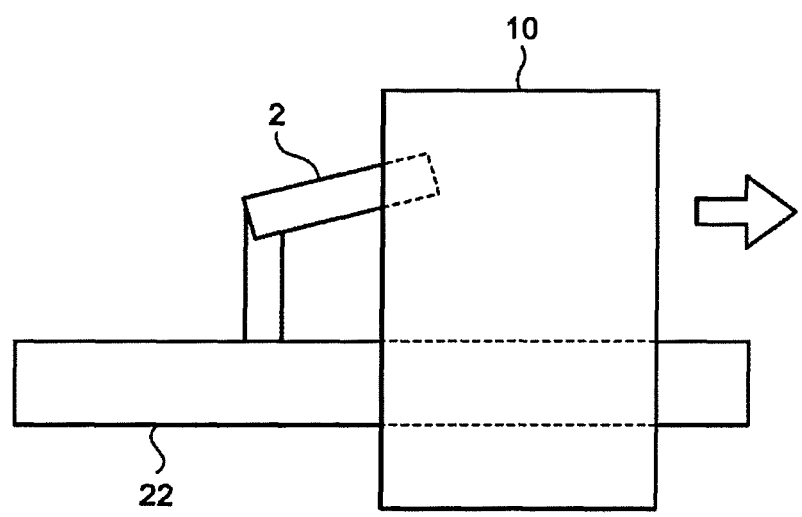
FIG. 8 is another drawing for explaining the second modification example of the first embodiment.
Figure 9:
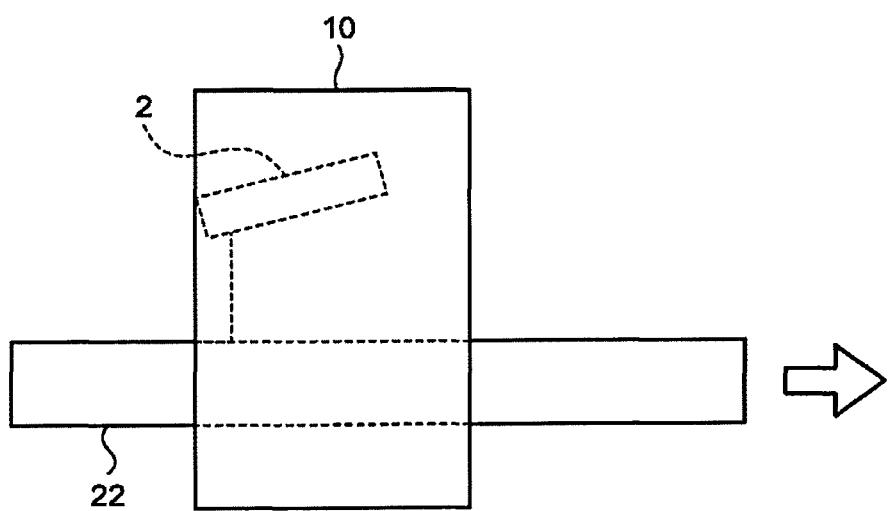
FIG. 9 is yet another drawing for explaining the second modification example of the first embodiment.

Thus, this modification example will be explained as a second modification example of the first embodiment. Some of the constituent elements that are the same as those in the first embodiment may be referred to by using the same reference characters, and the explanations thereof may be omitted. FIGS. 7 to 9 are drawings for explaining the second modification example of the first embodiment.

For example, as illustrated in the example in FIG. 7, when the gantry 10 is moved during the helical scan while the robot 2 is fixed to a floor surface 90, the relative positional relationship between the robot 2 and the gantry 10 changes during the helical scan. For this reason, it is possible to acquire volume data including the object 50 held by the robot 2, by performing the helical scan. Accordingly, when the gantry 10 is moved during the helical scan while the robot 2 is placed on the floor surface 90, the X-ray CT apparatus 1 may, at step S102, acquire three-dimensional CT image data as a result of the scan controlling function 34*e* causing the helical scan to be performed.

Further, as illustrated in the example in FIG. 8, also when the gantry 10 is moved during a helical scan while the robot 2 is fixed to the couchtop 22, the relative positional relationship between the robot 2 and the gantry 10 changes during the helical scan. Accordingly, also when the gantry 10 is moved during the helical scan while the robot 2 is fixed to the couchtop 22, the X-ray CT apparatus 1 may, at step S102, acquire three-dimensional CT image data as a result of the scan controlling function 34e causing the helical scan to be performed.

Further, as illustrated in the example in FIG. 9, also when the couchtop 22 is moved during a helical scan, while the robot 2 is fixed to the couchtop 22, the relative positional relationship between the robot 2 and the gantry 10 changes during the helical scan. Accordingly, also when the couchtop 22 is moved during the helical scan while the robot 2 is fixed to the couchtop 22, the X-ray CT apparatus 1 may, at step S102, acquire three-dimensional CT image data as a result of the scan controlling function 34e causing the helical scan to be performed.

Second Embodiment

Next, an image taking system according to a second embodiment will be explained. Some of the constituent elements that are the same as those in the first embodiment may be referred to by using the same reference characters, and the explanations thereof may be omitted. In the second embodiment, in addition to the various types of processes performed in the first embodiment, the X-ray CT apparatus 1 is configured to perform a correction data deriving process.

Figure 10:
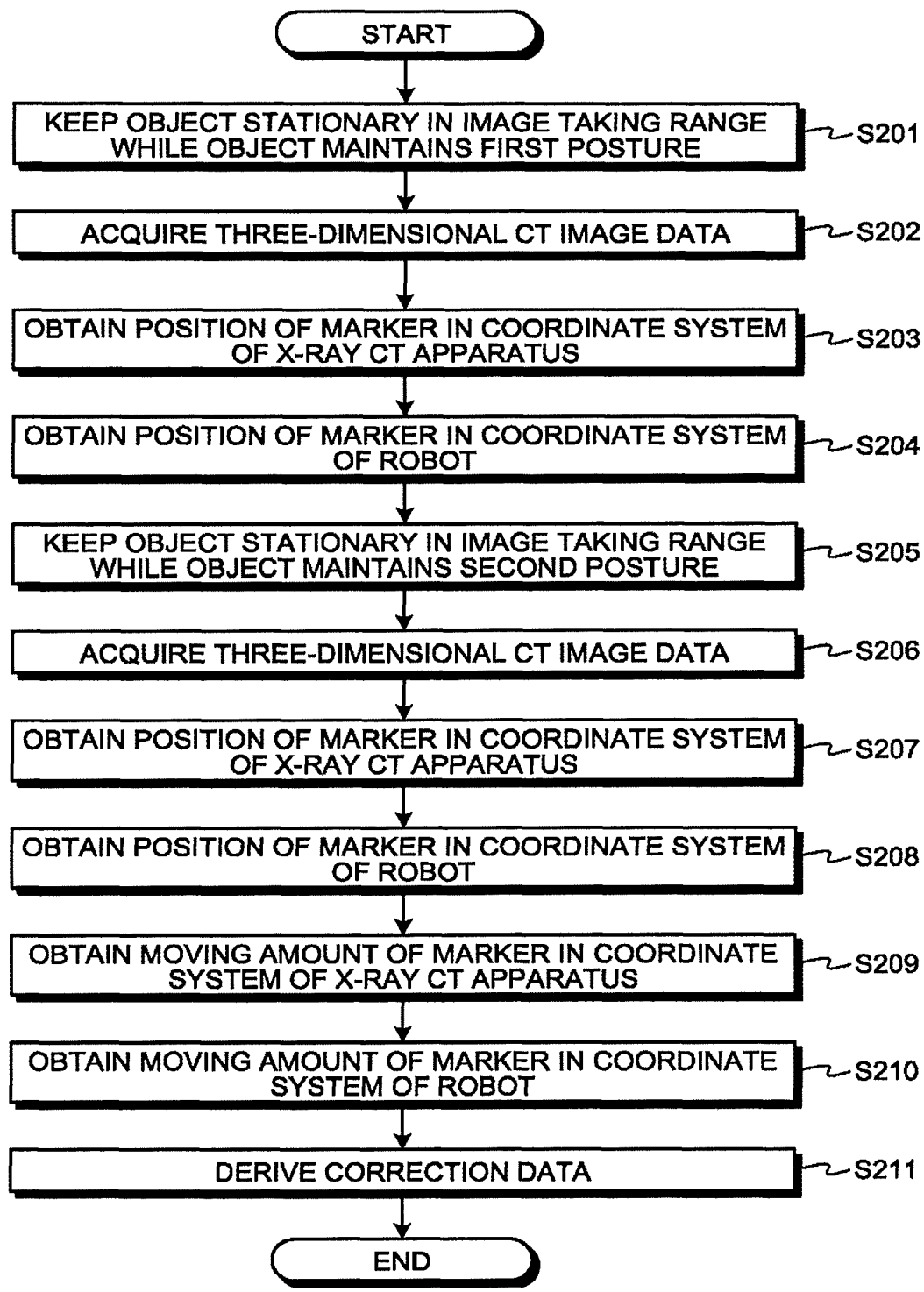
FIG. 10 is a flowchart illustrating a flow in an example of a correction data deriving process performed by an X-ray CT apparatus according to a second embodiment.

An example of the correction data deriving process performed by the X-ray CT apparatus 1 according to the second embodiment will be explained. FIG. 10 is a flowchart illustrating a flow in an example of the correction data deriving process performed by the X-ray CT apparatus 1 according to the second embodiment. The correction data deriving process is performed, for example, when the input interface 31 receives, from the user, an instruction to execute the correction data deriving process and further inputs the instruction to execute the correction data deriving process to the processing circuitry 34. When the correction data deriving process is to be executed, the patient P is not placed on the couch 20. Further, the correction data deriving process is an example of a process based on the medical image processing method.

As illustrated in FIG. 10, the robot controlling function 34g controls operations of the robot 2 so that the object 50 is kept stationary within an image taking range of the gantry 10 while maintaining a predetermined first posture, in such a manner that the object 50 held by the holding unit 2c of the robot 2 is positioned within the image taking range and is in the first posture (step S201).

Figure 11:
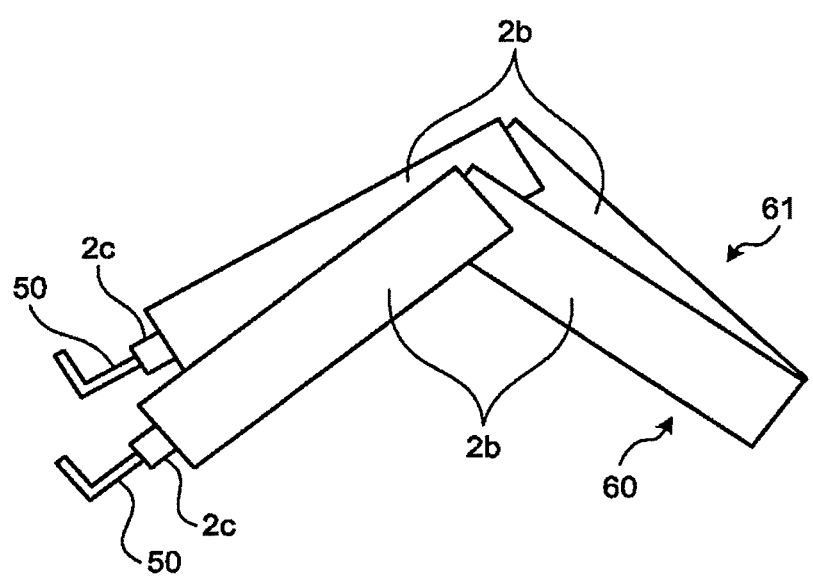
FIG. 11 is a drawing for explaining the correction data deriving process performed by the X-ray CT apparatus according to the second embodiment.

FIG. 11 is a drawing for explaining the correction data deriving process performed by the X-ray CT apparatus 1 according to the second embodiment. For example, at step S201, the robot controlling function 34g controls operations of the robot 2 so that the object 50 is kept stationary within the image taking range while maintaining a first posture 60, as illustrated in the example in FIG. 11.

Subsequently, the X-ray CT apparatus 1 acquires three-dimensional CT image data, as a result of the scan controlling function 34e causing a conventional scan to be performed on the object 50 that is kept stationary within the image taking range while maintaining the first posture 60 (step S202).

After that, the first obtaining function 34h obtains the position of the marker 50c within the coordinate system 1a, on the basis of the three-dimensional CT image data acquired at step S202 (step S203).

Subsequently, from the robot 2, the second obtaining function 34i obtains the position of the marker 50c of the object 50 that is kept stationary within the image taking range while maintaining the first posture 60, the position being expressed within the coordinate system 2d (step S204).

After that, the robot controlling function 34g controls operations of the robot 2 so that the object 50 is kept stationary within the image taking range of the gantry 10 while maintaining a predetermined second posture different from the first posture, so that the object 50 is positioned within the image taking range and is in the second posture (step S205).

For example, at step S205, the robot controlling function 34g controls operations of the robot 2 so that the object 50 is kept stationary in the image taking range while maintaining a second posture 61, as illustrated in the example in FIG. 11.

Subsequently, the X-ray CT apparatus 1 acquires three-dimensional CT image data, as a result of the scan controlling function 34e causing a conventional scan to be performed on the object 50 that is kept stationary within the image taking range while maintaining the second posture 61 (step S206).

After that, on the basis of the three-dimensional CT image data acquired at step S206, the first obtaining function 34h obtains the position of the marker 50c within the coordinate system 1a (step S207).

Subsequently, from the robot 2, the second obtaining function 34i obtains the position of the marker 50c of the object 50 that is kept stationary within the image taking range while maintaining the second posture 61, the position being expressed within the coordinate system 2d (step S208).

After that, the first obtaining function 34h obtains a moving amount of the marker 50c within the coordinate system 1a that is observed then the posture of the robot 2 is changed from the first posture 60 into the second posture 61 (step S209). For example, at step S209, the first obtaining function 34h calculates the distance between the position of the marker 50c within the coordinate system 1a obtained at step S203 and the position of the marker 50c within the coordinate system 1a obtained at step S207 and thus obtains the calculated distance as the moving amount of the marker 50c within the coordinate system 1a.

In this situation, the X-ray CT apparatus 1 is able to treat the moving amount of the marker 50c within the coordinate system 1a as the moving amount of the predetermined part 50b_1 within the coordinate system 1a. The moving amount of the marker 50c within the coordinate system 1a and the moving amount of the predetermined part 50b_1 within the coordinate system 1a are each an example of the first moving amount.

After that, the second obtaining function 34i obtains a moving amount of the marker 50c within the coordinate system 2d that is observed when the posture of the robot 2 is changed from the first posture 60 into the second posture 61 (step S210). For example, at step S210, the second obtaining function 34i calculates the distance between the position of the marker 50c within the coordinate system 2d obtained at step S204 and the position of the marker 50c within the coordinate system 2d obtained at step S208 and thus obtains the calculated distance as the moving amount of the marker 50c within the coordinate system 2d.

In this situation, the X-ray CT apparatus 1 is able to treat the moving amount of the marker 50c within the coordinate system 2d as the moving amount of the predetermined part 50b_1 within the coordinate system 2d. The moving amount of the marker 50c within the coordinate system 2d and the moving amount of the predetermined part 50b_1 within the coordinate system 2d are each an example of the second moving amount.

Subsequently, the deriving function 34j derives correction data used for correcting an error between the moving amount of the robot 2 within the coordinate system 1a and the moving amount of the robot 2 within the coordinate system 2d (step S211). For example, the deriving function 34j derives the correction data on the basis of the moving amount of the marker 50c within the coordinate system 1a obtained at step S209 and the moving amount of the marker 50c within the coordinate system 2d obtained at step S210.

For example, an example will be explained in which, at step S205 explained above, the robot controlling function 34g has arranged the posture of the robot 2 to be the second posture, by transmitting an instruction to the processing circuitry 2a_1 included in the robot 2 so as to indicate that the marker 50c should be moved 20 mm in the positive direction on the X-axis.

On the basis of an operation status of the driving mechanism 2a_2 and detection signals from the sensors attached to the robot arm 2b and to the holding unit 2c, the processing circuitry 2a_1 has learned the position of the marker 50c within the coordinate system 2d and the moving amount thereof in the positive direction on the X-axis. Further, upon determining that the marker 50c has moved 20.0 mm in the positive direction on the X-axis within the coordinate system 2d, the processing circuitry 2a_1 makes the robot 2 stationary. Accordingly, the moving amount of the marker 50c within the coordinate system 2d obtained at step S210 is 20.0 mm.

In this situation, let us discuss a situation in which the moving amount of the marker 50c within the coordinate system 1a obtained at step S209 is different from 20.0 mm and is 20.3 mm, for example. As an example, when the level of precision of either one of the sensors attached to the robot arm 2b and the holding unit 2c is not excellent, or the like, the marker 50c may move by a moving amount different from 20.0 mm, which is the designated moving amount. In that situation, the moving amount of the marker 50c within the coordinate system 1a obtained at step S209 is different from 20.0 mm.

To cope with this situation, at step S211, the deriving function 34j derives correction data calculated as, for example "the moving amount of the marker 50c within the coordinate system 2d obtained at step S210/the moving amount of the marker 50c within the coordinate system 1a obtained at step S209". For example, the deriving function 34j calculates the correction data as "20.0/20.3" where the symbol "/" is a division operator. The correction data can be used, for example, when the robot controlling function 34g moves the robot arm 2b or the holding unit 2c of the robot 2.

For instance, an example will be explained in which the input interface 31 has received, from the user, an instruction to move a predetermined part of the robot arm 2b by a predetermined distance D (mm) in the positive direction on the X-axis. In that situation, the robot controlling function 34g transmits an instruction indicating that the predetermined part of the robot arm 2b should be moved by "D×(20/20.3)" mm in the positive direction on the X-axis, to the processing circuitry 2a_1 included in the robot 2. Accordingly, the moving amount by which the predetermined part of the robot arm 2b moves becomes closer to the predetermined distance D designated by the user. Consequently, the X-ray CT apparatus 1 according to the second embodiment is further capable of inhibiting degradation in the level of precision of the moving control exercised on the robot 2.

Further, the X-ray CT apparatus 1 according to the second embodiment is capable of easily and conveniently aligning the coordinate system 1a and the coordinate system 2d with each other, similarly to the X-ray CT apparatus 1 according to the first embodiment.

Third Embodiment

Next, an image taking system according to a third embodiment will be explained. Some of the constituent elements that are the same as those in the first and/or the second embodiment may be referred to by using the same reference characters, and the explanations thereof may be omitted.

Figure 12:
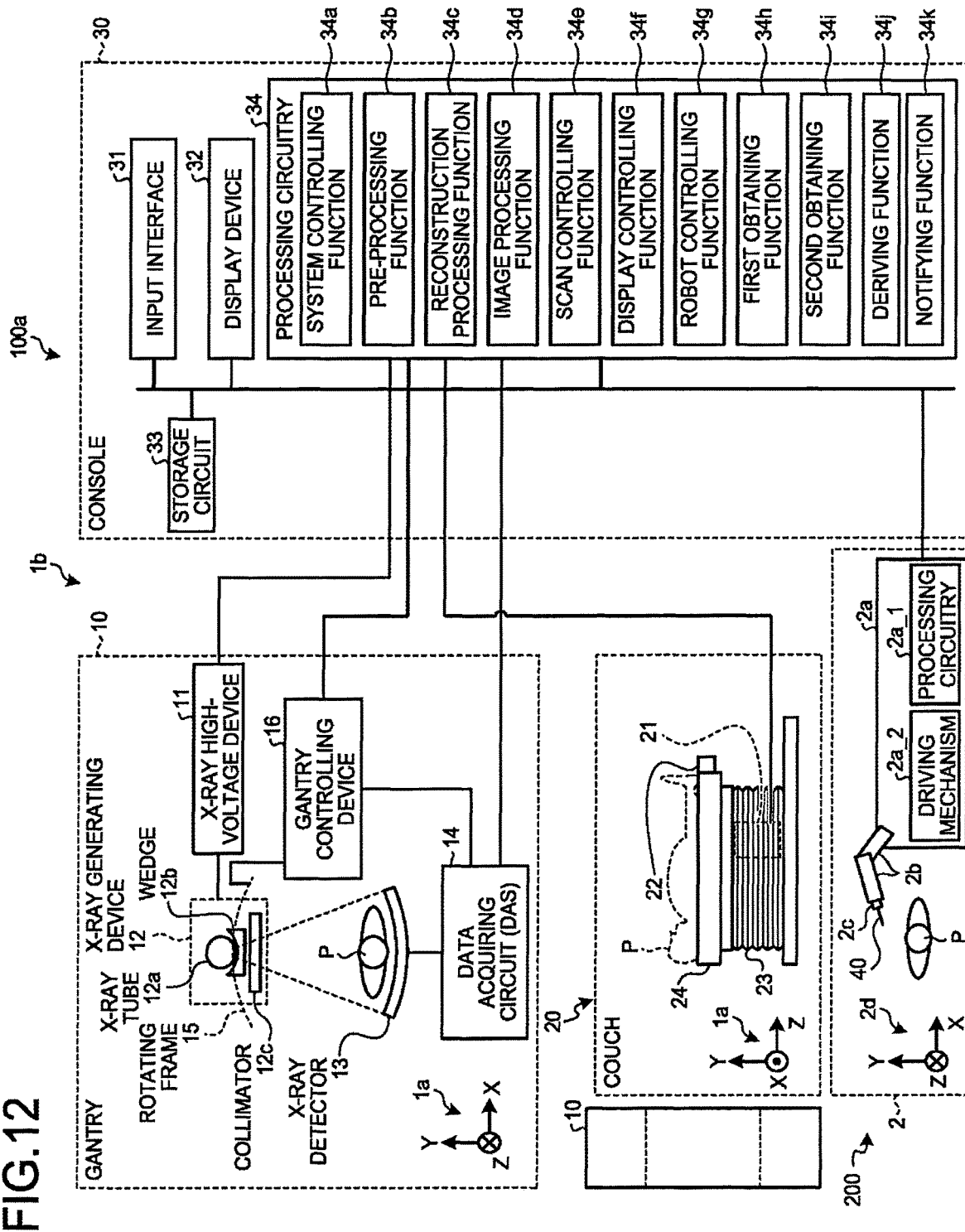
FIG. 12 is a diagram illustrating an exemplary configuration of an image taking system according to a third embodiment.

FIG. 12 is a diagram illustrating an exemplary configuration of an image taking system 100a according to the third embodiment. As illustrated in FIG. 12, the image taking system 100a includes an X-ray CT apparatus 1b and the robot 2.

The processing circuitry 34 of the X-ray CT apparatus 1b according to the third embodiment further includes a notifying function 34k, in addition to the configuration of the processing circuitry 34 of the X-ray CT apparatus 1 according to the first or the second embodiment. In other words, in the X-ray CT apparatus 1b according to the third embodiment, processes by the notifying function 34k are performed, in addition to the processes performed in the X-ray CT apparatus 1 according to the first or the second embodiment.

Figure 13:
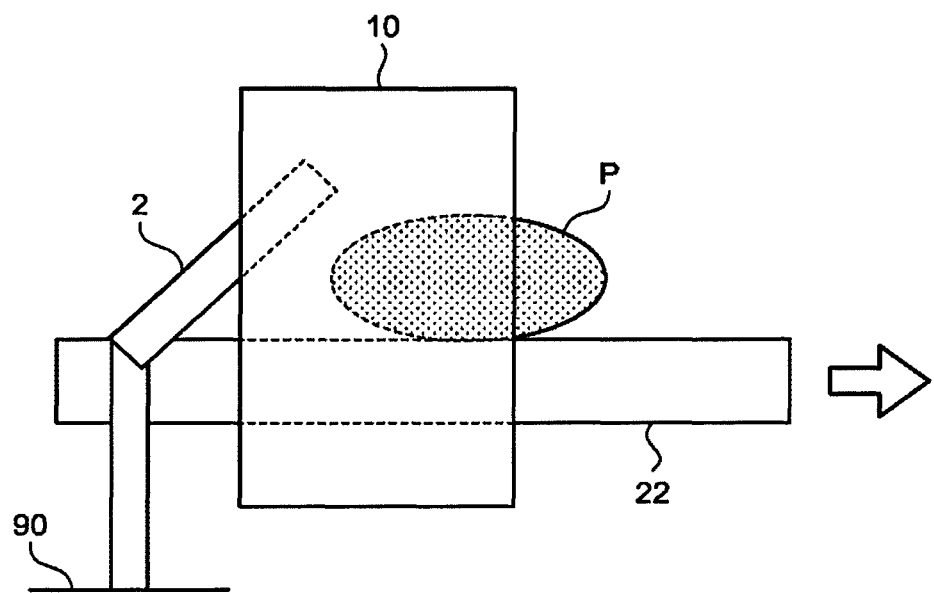
FIG. 13 is a drawing for explaining an example of processes performed by an X-ray CT apparatus according to the third embodiment.
Figure 14:
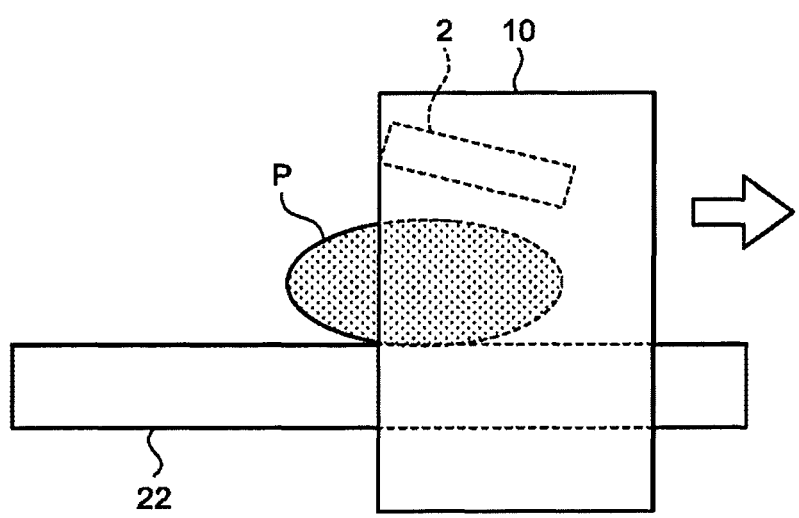
FIG. 14 is a drawing for explaining another example of the processes performed by the X-ray CT apparatus according to the third embodiment.
Figure 15:
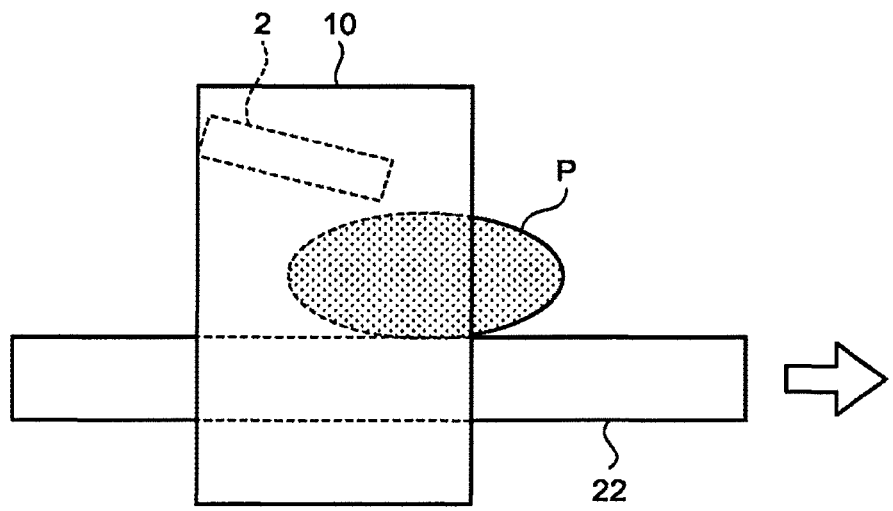
FIG. 15 is a drawing for explaining yet another example of the processes performed by the X-ray CT apparatus according to the third embodiment.

FIGS. 13 to 15 are drawings for explaining examples of the processes performed by the X-ray CT apparatus 1b according to the third embodiment. In the following sections, examples in which the robot 2 performs a manipulation such as a biopsy will be explained.

For example, as illustrated in the example in FIG. 13, when the couchtop 22 on which the patient P is placed is moved during the manipulation while the robot 2 is fixed to the floor surface 90, the relative positional relationship between the robot 2 and the couchtop 22 changes. When the relative positional relationship between the robot 2 and the couchtop 22 changes, the relative positional relationship between the robot 2 and the patient P also changes. Accordingly, when the relative positional relationship between the couchtop 22 and the robot 2 is changed due to the moving of the couchtop 22, the notifying function 34k calculates a moving amount of the couchtop 22 that is moved at the time of the change in the positional relationship. Further, the notifying function 34k notifies the processing circuitry 2a_1 included in the robot 2 of the calculated moving amount of the couchtop 22. The moving amount of the couchtop 22 is an example of the change amount in the positional relationship.

When being notified of the moving amount of the couchtop 22, the processing circuitry 2a_1 derives the position of the couchtop 22 observed after the relative positional relationship is changed, by adding the moving amount of the couchtop 22 indicated in the notification to the position of the couchtop 22 observed before the relative positional relationship is changed, within the coordinate system 2d. Accordingly, the processing circuitry 2a_1 is able to learn the position of the couchtop 22 observed after the relative positional relationship is changed. As a result, the robot 2 is able to learn the position of the patient P placed on the couchtop 22 observed after the relative positional relationship is changed.

In the example in FIG. 13, for example, when the distance between the couchtop 22 and the robot 2 is changed within the coordinate system 2*d* on at least one of the plurality of axes (i.e., the X-, the Y-, and the Z-axes) structuring the coordinate system 2*d*, the notifying function 34*k* performs the following process: The notifying function 34*k*, for example, provides a notification about a change amount in the distance between the couchtop 22 and the robot 2 as the moving amount of the couchtop 22.

Further, as illustrated in the example in FIG. 14, instead of the couchtop 22 on which the patient P is placed, when the gantry 10 is moved during the manipulation while the robot 2 is fixed to the gantry 10, the relative positional relationship between the robot 2 and the couchtop 22 changes. As a result, the relative positional relationship between the robot 2 and the patient P also changes. Accordingly, when the relative positional relationship between the couchtop 22 and the robot 2 is changed due to the moving of the gantry 10 to which the robot 2 is fixed, the notifying function 34*k* calculates a moving amount of the gantry 10 that is moved at the time of the change in the positional relationship. Further, the notifying function 34*k* notifies the processing circuitry 2*a*_1 included in the robot 2 of the calculated moving amount of the gantry 10. The moving amount of the gantry 10 is an example of the change amount in the positional relationship.

When being notified of the moving amount of the gantry 10, the processing circuitry 2*a*_1 derives the position of the couchtop 22 observed after the relative positional relationship is changed, on the basis of the position of the couchtop 22 observed before the relative positional relationship is changed and the moving amount of the gantry 10 indicated in the notification, within the coordinate system 2*d*. Accordingly, the processing circuitry 2*a*_1 is able to learn the position of the couchtop 22 observed after the relative positional relationship is changed. As a result, the robot 2 is able to learn the position of the patient P placed on the couchtop 22 observed after the relative positional relationship is changed.

In the example illustrated in FIG. 14 where the gantry 10 is moved, for example, when the distance between the couchtop 22 and the robot 2 is changed within the coordinate system 2*d* on at least one of the plurality of axes structuring the coordinate system 2*d* (situation 1), the notifying function 34*k* performs the following process: The notifying function 34*k*, for example, provides a notification about a change amount in the distance between the couchtop 22 and the robot 2 as the moving amount of the gantry 10.

Further, in the example illustrated in FIG. 14 where the gantry 10 is moved, for example, when the rotation angle of the robot 2 is changed within the coordinate system 2*d* with respect to the rotation angle of the couchtop 22 around at least one of the plurality of axes structuring the coordinate system 2*d* (situation 2), the notifying function 34*k* performs the following process: The notifying function 34*k*, for example, provides a notification about a change amount in the rotation angle of the robot 2 with respect to the rotation angle of the couchtop 22, as the moving amount of the gantry 10.

In other words, when at least one selected from between situation 1 and situation 2 occurs, the notifying function 34*k* notifies the robot 2 of at least one selected from between the change amount in the distance and the change amount in the rotation angle.

Further, as illustrated in the example in FIG. 15, when the couchtop 22 on which the patient P is placed is moved during the manipulation while the robot 2 is fixed to the gantry 10, the relative positional relationship between the robot 2 and the couchtop 22 changes. As a result, the relative positional relationship between the robot 2 and the patient P also changes. Accordingly, when the relative positional relationship between the couchtop 22 and the robot 2 is changed due to the moving of the couchtop 22, the notifying function 34*k* calculates a moving amount of the couchtop 22 that is moved at the time of the change in the positional relationship. Further, the notifying function 34*k* notifies the processing circuitry 2*a*_1 included in the robot 2 of the calculated moving amount of the couchtop 22.

In the example illustrated in FIG. 15 where the couchtop 22 is moved, for example, when the distance between the couchtop 22 and the robot 2 is changed within the coordinate system 2*d* on at least one of the plurality of axes structuring the coordinate system 2*d* (situation 3), the notifying function 34*k* performs the following process: The notifying function 34*k*, for example, provides a notification about a change amount in the distance between the couchtop 22 and the robot 2 as the moving amount of the couchtop 22.

Further, in the example illustrated in FIG. 15 where the couchtop 22 is moved, for example, when the rotation angle of the robot 2 is changed with respect to the rotation angle of the couchtop 22 within the coordinate system 2*d*, on at least one of the plurality of axes structuring the coordinate system 2*d* (situation 4), the notifying function 34*k* performs the following process: The notifying function 34*k*, for example, provides a notification about a change amount in the rotation angle of the robot 2 with respect to the rotation angle of the couchtop 22, as the moving amount of the couchtop 22.

In other words, when at least one selected from between situation 3 and situation 4 occurs, the notifying function 34*k* notifies the robot 2 of at least one selected from between the change amount in the distance and the change amount in the rotation angle.

As explained above, when the relative positional relationship between the robot 2 and the patient P is changed, the X-ray CT apparatus 1*b* according to the third embodiment is configured to notify the robot 2 of one selected from between the moving amount of the gantry 10 and the moving amount of the couchtop 22. Consequently, even when the relative positional relationship between the robot 2 and the patient P is changed, the X-ray CT apparatus 1*b* according to the third embodiment is capable of enabling the robot 2 to learn the position of the patient P observed after the relative positional relationship is changed.

The X-ray CT apparatus 1 according to the third embodiment is capable of easily and conveniently aligning the coordinate system 1*a* and the coordinate system 2*d* with each other, similarly to the X-ray CT apparatus 1 according to the first embodiment and the X-ray CT apparatus 1 according to the second embodiment.

Fourth Embodiment

The processing circuitry 2*a*_1 of the robot 2 may include functions that are the same as the first obtaining function 34*h*, the second obtaining function 34*i*, and the deriving function 34*j* described above. Thus, this embodiment will be explained as a fourth embodiment. Some of the constituent elements that are the same as those in the first embodiment, the second embodiment, and/or the third embodiment may be referred to by using the same reference characters, and the explanations thereof may be omitted.

An image taking system according to the fourth embodiment has the same configuration as that of the image taking system 100 according to the first or the second embodiment or that of the image taking system 100a according to the third embodiment. It should be noted, however, that the processing circuitry 34 does not necessarily have to include the first obtaining function 34h, the second obtaining function 34i, and the deriving function 34j.

Figure 16:
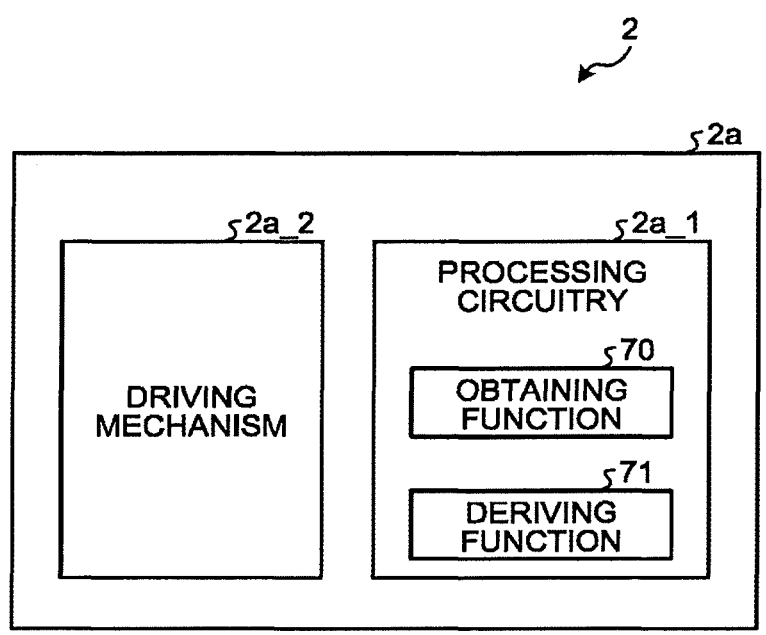
FIG. 16 is a diagram illustrating an exemplary configuration of a robot main body of a robot according to a fourth embodiment.

FIG. 16 is a drawing illustrating an exemplary configuration of a robot main body 2a of the robot 2 according to the fourth embodiment. The processing circuitry 2a_1 of the robot main body 2a according to the fourth embodiment includes an obtaining function 70 and a deriving function 71.

The processing circuitry 2a_1 according to the fourth embodiment is configured to further execute processes performed by the obtaining function 70 and processes performed by the deriving function 71, in addition to the processes executed by the processing circuitry 2a_1 according to the first, the second, or the third embodiment.

In the fourth embodiment, of the coordinate system aligning process illustrated in FIG. 6, the robot controlling function 34g performs the process at step S101, whereas the scan controlling function 34e performs the process at step S102. Further, the scan controlling function 34e transmits the three-dimensional CT image data acquired as a result of the process at step S102, to the processing circuitry 2a_1.

Subsequently, by using the three-dimensional CT image data transmitted at step S102, the obtaining function 70 performs the same processes as those at steps S103 through S105 explained above. The obtaining function 70 is an example of an obtaining unit.

After that, by performing the same process as the process at step S109 explained above, the deriving function 71 derives information that brings the coordinate system 1a and the coordinate system 2d into correspondence with each other. Subsequently, the deriving function 71 notifies the X-ray CT apparatus 1 of the information that brings the coordinate system 1a and the coordinate system 2d into correspondence with each other, so that the X-ray CT apparatus 1 arranges the coordinate system 1a to substantially coincide with the coordinate system 2d. The deriving function 71 is an example of a deriving unit.

In other words, the obtaining function 70 according to the fourth embodiment is configured to obtain the position of the predetermined part 50b_1 of the object 50, the direction of the rotation axis 50h of the object 50, and the rotation angle of the object 50 within the coordinate system 1a, on the basis of the three-dimensional CT image data acquired by imaging the object 50 held by the robot 2. Further, the deriving function 71 according to the fourth embodiment derives the information that brings the coordinate system 1a and the coordinate system 2d into correspondence with each other, on the basis of the position, the direction, the rotation angle obtained by the obtaining function 70, as well as the position of the predetermined part 50b_1, the direction of the rotation axis 50h, and the rotation angle of the object 50 within the coordinate system 2d.

The X-ray CT apparatus according to the fourth embodiment is capable of easily and conveniently aligning the coordinate system 1a and the coordinate system 2d with each other, similarly to the X-ray CT apparatus 1 according to the first embodiment and the like.

In the image taking system 100 or the image taking system 100a, another arrangement is acceptable in which, while a workstation is connected to the X-ray CT apparatus 1, the workstation is configured to have the same functions as those of the first obtaining function 34h, the second obtaining function 34i, and the deriving function 34j described above. Further, it is also acceptable to configure the workstation to have the same functions as the obtaining function 70 and the deriving function 71 described above.

Further, in the embodiments described above, the robot 2 is arranged to hold the object 50, when the coordinate system aligning process and the correction data deriving process are performed. Further, in the embodiments described above, the coordinate system aligning process and the correction data deriving process are performed by using the three-dimensional CT image data acquired by imaging the object 50.

However, another arrangement is also acceptable in which the robot 2 has formed therewith a member having the same shape as that of the object 50, as a member constituting a part of the robot 2. For example, the robot arm 2b may have formed therewith a member having the same shape as that of the object 50. Further, in the embodiments described above, the markers 50c, 50d, and 50f are attached to the predetermined parts 50a_1, 50b_1, and 50b_2 of the object 50, respectively. However, a plurality of markers may similarly be pasted onto a plurality of predetermined parts (parts in at least three locations) of the robot 2. For example, the plurality of markers may be pasted onto a plurality of predetermined parts of the robot arm 2b. In this situation, as explained in the embodiments above, the plurality of markers are not positioned on mutually the same straight line. Further, it is sufficient when the positional relationship among the plurality of markers provided in at least three locations is an axially asymmetric positional relationship. Further, the first obtaining function 34h, the second obtaining function 34i, and the deriving function 34j may perform the coordinate system aligning process and the correction data deriving process by using three-dimensional CT image data acquired by imaging the robot 2 described above, in place of the object 50.

When the robot arm 2b has formed therewith the member that has the same shape as that of the object 50, or when the plurality of markers are pasted on the robot arm 2b, the first obtaining function 34h, the second obtaining function 34i, and the deriving function 34j may perform processes by using the data described below. For example, the first obtaining function 34h, the second obtaining function 34i, and the deriving function 34j may perform the coordinate system aligning process and the correction data deriving process by using three-dimensional CT image data acquired by imaging the robot arm 2b. The robot arm 2b is an example of the image taking target.

Similarly, the obtaining function 70 and the deriving function 71 may perform the coordinate system aligning process and the correction data deriving process by using three-dimensional CT image data acquired by imaging the robot 2 described above. The robot 2 is an example of the peripheral device and is an example of the image taking target.

When the robot arm 2b has formed therewith the member that has the same shape as that of the object 50, or when the plurality of markers are pasted on the robot arm 2b, the obtaining function 70 and the deriving function 71 may perform processes by using the data described below. For example, the obtaining function 70 and the deriving function 71 may perform the coordinate system aligning process and the correction data deriving process by using three-dimensional CT image data acquired by imaging the robot arm 2b.

According to at least one aspect of the embodiments described above, it is possible to easily and conveniently align the coordinate system 1a and the coordinate system 2d with each other.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising processing circuitry configured:
    to obtain a first position of a predetermined part of an image taking target, a first direction of a rotation axis of the image taking target, and a first rotation angle of the image taking target, within a coordinate system of the medical image diagnosis apparatus, on a basis of image data acquired by imaging the image taking target that is one selected from between a robot arm included in a medical robot system and holding a medical tool and an object held by the robot arm;
    to obtain a second position of the predetermined part, a second direction of the rotation axis, and a second rotation angle of the image taking target, within a coordinate system of the medical robot system; and
    to derive information that brings the coordinate system of the medical image diagnosis apparatus and the coordinate system of the medical robot system into correspondence with each other, on a basis of the first position, the first direction, the first rotation angle, the second position, the second direction, and the second rotation angle.

2. The medical image diagnosis apparatus according to claim 1, wherein the processing circuitry obtains the first position, the first direction, and the first rotation angle, on the basis of the image data acquired by imaging a plurality of markers that are provided in at least three locations of the image taking target and that are not positioned on a mutually same straight line.

3. The medical image diagnosis apparatus according to claim 2, wherein a positional relationship among the plurality of markers is an axially asymmetric positional relationship.

4. The medical image diagnosis apparatus according to claim 1, wherein the processing circuitry obtains the first position, the first direction, and the first rotation angle on a basis of three-dimensional CT image data acquired by imaging the image taking target.

5. The medical image diagnosis apparatus according to claim 1, wherein
    the processing circuitry further obtains a first moving amount of the predetermined part within the coordinate system of the medical image diagnosis apparatus, the first moving amount being observed when a posture of the robot arm is changed from a first posture to a second posture that is different from the first posture, on a basis of two pieces of image data acquired by imaging the image taking target when the robot arm is in the first posture and when the robot arm is in the second posture,
    the processing circuitry further obtains a second moving amount of the predetermined part within the coordinate system of the medical robot system, the second moving amount being observed when the posture of the robot arm is changed from the first posture to the second posture, and
    on a basis of the first moving amount and the second moving amount, the processing circuitry further derives correction data used for correcting an error between a moving amount of the robot arm within the coordinate system of the medical image diagnosis apparatus and a moving amount of the robot arm within the coordinate system of the medical robot system.

6. The medical image diagnosis apparatus according to claim 1, further comprising a couchtop on which a patient may be placed, wherein when a relative positional relationship between the couchtop and the medical robot system is changed, the processing circuitry notifies the medical robot system of a change amount in the positional relationship.

7. The medical image diagnosis apparatus according to claim 6, wherein, when at least one of the following two is changed within the coordinate system of the medical image diagnosis apparatus due to either moving of the couchtop or moving of a gantry to which the robot arm is fixed: (i) a distance between the couchtop and the robot arm on at least one of a plurality of axes structuring the coordinate system of the medical image diagnosis apparatus; and (ii) a rotation angle of the robot arm with respect to a rotation angle of the couchtop around at least one of the plurality of axes, the processing circuitry notifies the medical robot system of at least one selected from between a change amount in the distance between the couchtop and the robot arm and a change amount in the rotation angle of the robot arm with respect to the rotation angle of the couchtop.

8. The medical image diagnosis apparatus according to claim 1, wherein the processing circuitry derives the information by arranging the first position and the second position to coincide with each other, arranging the first direction and the second direction to coincide with each other, and arranging the first rotation angle and the second rotation to coincide with each other.

9. A medical image processing method comprising:
    obtaining a first position of a predetermined part of an image taking target, a first direction of a rotation axis of the image taking target, and a first rotation angle of the image taking target, within a coordinate system of a medical image diagnosis apparatus, on a basis of image data acquired by imaging the image taking target that is one selected from between a robot arm included in a medical robot system and holding a medical tool and an object held by the robot arm;
    obtaining a second position of the predetermined part, a second direction of the rotation axis, and a second rotation angle of the image taking target, within a coordinate system of the medical robot system; and
    deriving information that brings the coordinate system of the medical image diagnosis apparatus and the coordinate system of the medical robot system into correspondence with each other, on a basis of the first position, the first direction, the first rotation angle, the second position, the second direction, and the second rotation angle.

10. The medical image processing method according to claim 9, comprising obtaining the first position, the first direction, and the first rotation angle, on the basis of the image data acquired by imaging a plurality of markers that are provided in at least three locations of the image taking target and that are not positioned on a mutually same straight line.

11. The medical image processing method according to claim 10, wherein a positional relationship among the plurality of markers is an axially asymmetric positional relationship.

12. The medical image processing method according to claim 9, comprising obtaining the first position, the first direction, and the first rotation angle on a basis of three-dimensional CT image data acquired by imaging the image taking target.

13. The medical image processing method according to claim 9, comprising:
- obtaining a first moving amount of the predetermined part within the coordinate system of the medical image diagnosis apparatus, the first moving amount being observed when a posture of the robot aim is changed from a first posture to a second posture that is different from the first posture, on a basis of two pieces of image data acquired by imaging the image taking target when the robot arm is in the first posture and when the robot ai rn is in the second posture,
- obtaining a second moving amount of the predetermined part within the coordinate system of the medical robot system, the second moving amount being observed when the posture of the robot arm is changed from the first posture to the second posture, and
- on a basis of the first moving amount and the second moving amount, deriving correction data used for correcting an error between a moving amount of the robot arm within the coordinate system of the medical image diagnosis apparatus and a moving amount of the robot arm within the coordinate system of the medical robot system.

14. The medical image processing method according to claim 9, wherein the medical image diagnosis apparatus comprises a couchtop, the method further comprising, when a relative positional relationship between the couchtop and the medical robot system is changed, notifying the medical robot system of a change amount in the positional relationship.

15. The medical image processing method according to claim 14, comprising, when at least one of the following two is changed within the coordinate system of the medical image diagnosis apparatus due to either moving of the couchtop or moving of a gantry to which the robot arm is fixed: (i) a distance between the couchtop and the robot arm on at least one of a plurality of axes structuring the coordinate system of the medical image diagnosis apparatus; and (ii) a rotation angle of the robot min with respect to a rotation angle of the couchtop around at least one of the plurality of axes, notifying the medical robot system of at least one selected from between a change amount in the distance between the couchtop and the robot arm and a change amount in the rotation angle of the robot arm with respect to the rotation angle of the couchtop.

16. The medical image processing method according to claim 9, comprising deriving the information by arranging the first position and the second position to coincide with each other, arranging the first direction and the second direction to coincide with each other, and arranging the first rotation angle and the second rotation to coincide with each other.

* * * * *

UNITED STATES PATENT AND TRADEMARK OFFICE
CERTIFICATE OF CORRECTION

PATENT NO. : 10,874,365 B2
APPLICATION NO. : 16/233190
DATED : December 29, 2020
INVENTOR(S) : Masaharu Tsuyuki Page 1 of 1

It is certified that error appears in the above-identified patent and that said Letters Patent is hereby corrected as shown below:

In the Claims

In Claim 13 at Column 27, Line 15 "aim" should read --arm--

In Claim 13 at Column 27, Line 19 "ai rn" should read --arm--

In Claim 15 at Column 28, Line 17 "min" should read --arm--

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*